(12) United States Patent
Margel et al.

(10) Patent No.: US 9,295,736 B2
(45) Date of Patent: Mar. 29, 2016

(54) POLYMER NANOPARTICLES COATED BY MAGNETIC METAL OXIDE AND USES THEREOF

(75) Inventors: Shlomo Margel, Rehovot (IL); Benny Perlstein, Ra'anana (IL); Chaya Brodie, Southfield, MI (US); Tom Mikkelsen, West Bloomfield, MI (US)

(73) Assignees: Bar Ilan University, Ramat Gan (IL); Henry Ford Health System, Detroit, MI (US)

( * ) Notice: Subject to any disclaimer, the term of this patent is extended or adjusted under 35 U.S.C. 154(b) by 952 days.

(21) Appl. No.: 12/232,818

(22) Filed: Sep. 24, 2008

(65) Prior Publication Data

US 2009/0110644 A1 Apr. 30, 2009

Related U.S. Application Data

(60) Provisional application No. 60/960,270, filed on Sep. 24, 2007.

(51) Int. Cl.
| | |
|---|---|
| *A61K 49/18* | (2006.01) |
| *A61K 41/00* | (2006.01) |
| *A61K 47/48* | (2006.01) |
| *B82Y 5/00* | (2011.01) |

(52) U.S. Cl.
CPC ......... *A61K 49/1878* (2013.01); *A61K 41/0052* (2013.01); *A61K 47/48238* (2013.01); *A61K 47/48853* (2013.01); *A61K 47/48861* (2013.01); *A61K 47/48907* (2013.01); *A61K 49/1866* (2013.01); *B82Y 5/00* (2013.01)

(58) Field of Classification Search
CPC ................................................. A61K 49/1878
See application file for complete search history.

(56) References Cited

U.S. PATENT DOCUMENTS

| | | | |
|---|---|---|---|
| 5,543,332 A | 8/1996 | Lihme et al. | |
| 5,834,121 A | 11/1998 | Sucholeiki et al. | |
| 5,855,987 A | 1/1999 | Margel et al. | |
| 6,998,116 B1 * | 2/2006 | Ashkenazi | 424/85.1 |
| 7,368,295 B2 | 5/2008 | Tovar et al. | |
| 7,550,282 B2 | 6/2009 | Margel et al. | |
| 2002/0076409 A1 * | 6/2002 | March et al. | 424/145.1 |
| 2003/0032995 A1 * | 2/2003 | Handy et al. | 607/103 |
| 2004/0265392 A1 | 12/2004 | Tovar et al. | |
| 2005/0090732 A1 * | 4/2005 | Ivkov et al. | 600/411 |
| 2005/0129769 A1 * | 6/2005 | Barry et al. | 424/486 |
| 2005/0226913 A1 | 10/2005 | Bringley et al. | |
| 2008/0206229 A1 * | 8/2008 | Ono et al. | 424/130.1 |
| 2009/0110644 A1 | 4/2009 | Margel et al. | |
| 2009/0311192 A1 | 12/2009 | Margel et al. | |

FOREIGN PATENT DOCUMENTS

| | | |
|---|---|---|
| EP | 1088315 B1 | 6/2003 |
| EP | 1556076 | 7/2005 |
| JP | 2002517085 A | 6/2002 |
| JP | 2005504066 A | 2/2005 |
| JP | 2005521640 A | 7/2005 |
| JP | 2005535604 A | 11/2005 |
| JP | 2006514096 A | 4/2006 |
| JP | 2007523067 A | 8/2007 |
| WO | WO 98/02189 | 5/1998 |
| WO | WO 99/62079 | 12/1999 |
| WO | WO 9962079 A1 * | 12/1999 |
| WO | WO03020320 A2 | 3/2003 |
| WO | WO03042344 A2 | 5/2003 |
| WO | WO03101425 A2 | 12/2003 |
| WO | WO04001009 | 12/2003 |
| WO | WO2004050895 A2 | 6/2004 |
| WO | WO 2005/017539 | 2/2005 |
| WO | WO2005072893 A1 | 8/2005 |
| WO | WO2006/029275 A2 | 3/2006 |
| WO | WO 2006/106513 | 10/2006 |
| WO | WO 2007/072982 | 6/2007 |
| WO | WO 2009/040811 | 4/2009 |

OTHER PUBLICATIONS

Sorimachi, K., et al., "Alternative Medicine Safety: Agaricus blazei and Propolis", 2011, Combinatorial Chemistry and High Throughput Screening, 14, pp. 616-621.*
Kagawa, S., et al., Antitumor Activity and Bystander Effects of the Tumor Necrosis Factor-related Apoptosis-inducing Ligand (TRAIL) Gene, 2001, Cancer Research, 61, pp. 3330-3338.*
Bilkova, Z., et al., "Enzymes immobilized on magnetic carriers: efficient and selective system for protein modification" 2002, Journal of Chromotography B, 770, pp. 177-181.*
Liao, M., et al., "Immobilization of yeast alcohol dehydrogenase on magnetic nanoparticles for improving its stability", 2001, Biotechnology Letters, 23, pp. 1723-1727.*
Mateo, C., et al., "Improvement of enzyme activity, stability and selectivity via immobilization techniques", 2007, Enzyme and Microbial Technology 40, pp. 1451-1463.*
Rowinsky, E., et al., "Targeted Induction of Apoptosis in Cancer Management: The Emerging Role of Tumor Necrosis Factor-Related Apoptosis-Inducing Ligand Receptor Activating Agents" 2005, Journal oof Clinical Oncology, 23, pp. 9394-9407.*

(Continued)

*Primary Examiner* — Michael G Hartley
*Assistant Examiner* — Lance Rider
(74) *Attorney, Agent, or Firm* — Roach Brown McCarthy & Gruber, P.C.; Kevin D. McCarthy

(57) ABSTRACT

The invention provides nanoparticles consisting of a polymer which is a metal chelating agent coated with a magnetic metal oxide, wherein at least one active agent is covalently bound to the polymer, said nanoparticles may optionally further comprise at least one active agent physically or covalently bound to the outer surface of the magnetic metal oxide. Pharmaceutical compositions comprising these nanoparticles may be used, inter alia, for detection and treatment of tumors and inflammations.

31 Claims, 22 Drawing Sheets
(16 of 22 Drawing Sheet(s) Filed in Color)

(56) References Cited

OTHER PUBLICATIONS

Michael R. Bockstaller, et al., Size-Selective Organization of Enthalpic Compatibilized Nanocrystals in Ternary Block Copolymer/Particla Mixtures, vol. 125, No. 18, 2003 pp. 5276-5277.

B. C. Bunker et al., Ceramic Thin-Film Formation on Functionalized Interfaces Through Biomimetic Processingvol. 264 Apr. 1, 1994 pp. 48-55.

Anna Galperin et al., Radiopaque iodinated polymeric nanoparticles for X-ray imaging applications, (2007) pp. 4461-4468.

T. Green-Sadan et al., Glial cell line-derived neurotrophic factor-conjugated nanoparticles suppress acquisition of cocaine self-administration in rats 194 (2005) pp. 97-105.

R. Hergt et al., Maghemite nanoparticles with very high AC-losses for application in RF-magnetic hyperthermia 270 (2004) pp. 345-357.

J. Lacoste, et al., Gamma-, Photo-, and Thermally-Initiated Oxidation of Isotactic Polypropylene pp. 715-722.

Leemputten et al., Biotechnology and Bioengineering bol XVI (1974) pp. 997-1600.

Michael J. Szymonifka, et al., Magnetically Manipulable Polymeric Supports for Solid Phase Organic Synthesis, vol. 36, No. 10, pp. 1597-1600, 1995.

Kircher Mortiz F et al: "A dual flurochrome probe for imaging proteases" Bioconjugate Chemistry, vol. 15, No. 2, Mar. 1, 2004, pp. 242-248.

Josephson Lee et al: "Near-infrared fluorescent nanoparticles as combined MR/optical imaging probes" Bioconjugate Chemistry, vol. 13, No. 3, May 1, 2002, pp. 554-560.

Zimmer Claus et al: "MR imaging of phagocytosis in experimental gliomas" Radiology, vol. 197, No. 2, 1995, pp. 533-538.

International Search Report of corresponding International Application No. PCT/IL2008/001286, dated Dec. 9, 2009.

Perlstein B et al., "Synthesis and characterization of functionalized magnetic maghemite nanoparticles with fluorescent probe capabilities for biological applications," Journal of Biomedical Materials Research Part B: Applied Biomaterials, vol. 92B, Iss. 2, pp. 353-360, Feb. 2010.

Sung, Li-Piin, et al., "Characterization of Metal-Oxide Nanoparticles: Synthesis and Dispersion in Polymeric Coatings," Mat. Res. Soc. Symp. Proc. vol. 740, 2003 Materials Research Society, pp. I5.4.0-I5.4.6.

Sindhu, S. et al., "Synthesis and characterization of ferrite nanocomposite spheres from hydroxylated polymers," Journal of Magnetism and Magnetic Materials 296 (2006) 104-113.

Wizel S., et al., "The preparation of metal-polymer composite materials using ultrasound radiation: Part II. Differences in physical properties of cobalt-polymer and iron-polymer composites," J. Mater. Res., vol. 14, No. 10, Oct. 1999, pp. 3913-3920.

Zhang H. et al., "Establishment and implications of a characterization method for magnetic nanoparticle using cell tracking velocimetry and magnetic susceptibility modified solutions," Analyst, 2005, 130, 514-527.

Ziv O. et al., "Immunogenicity of bioactive magnetic nanoparticles: Natural and acquired antibodies," Journal of Biomedical Materials Research Part A, 2007, pp. 1011-1021.

Sinyakov M. et al., "Nano- and microparticles as adjuvants in vaccine design: Success and failure is related to host natural antibodies," Vaccine 24 (2006) 6534-6541.

Fan X. et al., "Surface-initiated polymerization from $TiO_2$ nanoparticle surfaces through a biomimetic initiator: A new route toward polymer-matrix nanocomposites," Composites Science and Technology 66 (2006) 1198-1204.

Drew C. et al., "Metal Oxide-Coated Polymer Nanofibers," Nano Lett., vol. 3, No. 2, 2003, pp. 143-147.

Boguslavsky, L., et al.., "Synthesis and characterization of polyacrylonitrile nanoparticles by dispersion/emulsion polymerization process," Journal of Colloid and Interface Science 289 (2005) 71-85.

Balazs A. et al., "Nanoparticle Polymer Composites: Where Two Small Worlds Meet," Science, vol. 314, Nov. 17, 2006, pp. 1107-1110.

Yu S., et al., "Carboxyl group ($-CO_2H$) functionalized ferrimagnetic iron oxide nanoparticles for potential bio-applications," J. Mater. Chem., 2004, 1 4, 2781-2786.

Gupta A. et al., "Synthesis and surface engineering of iron oxide nanoparticles for biomedical applications," Biomaterials 26 (2005) 3995-4021.

Gao X., et al., "In vivo cancer targeting and imaging with semiconductor quantum dots," Nature Biotechnology, vol. 22:8, Aug. 2004, 969-976.

Caruso F., "Nanoengineering of Particle Surfaces," Adv. Mater. 2001, 13, No. 1, pp. 11-22.

Weizhong Wei et al., "Magnetic Iron Oxide Nanoparticles Mediated Gene Therapy For Breast Cancer—An In Vitro Study", Journal Of Huazhong University Of Science And Technology, vol. 26, No. 6, pp. 728-730 (2006).

Saito R. et al., "Convection-Enhanced Delivery Of Tumor Necrosis Factor-Related Apoptosis-Inducing Ligand With Systemic Administration Of Temozolomide Prolongs Survival In An Intracranial Glioblastoma Xenograft Model", Cancer Research, vol. 64, No. 19, pp. 6858-6862, (2004).

Wilfried Roth et al., "Locoregional Apo2L/TRAIL Eradicates Intracranial Human Malignant Glioma Xenografts In Athymic Mice In The Absence Of Neurotoxicity", Biochemical And Biophysical Research Communications, vol. 265, No. 2, pp. 479-483 (1999).

Susanne Bryde et al., "Tumor Necrosis Factor (TNF)-Functionalized Nanostructured Particles for the Stimulaion of Membrane TNF-Specific Cell Responses", Bioconjugate Chem., vol. 16, No. 6, pp. 1459-1467 (2005).

Sun-Shin Cha et al., "Crystal Structure of TRAIL-DR5 Complex Identifies a Critical Role of the Unique Frame Insertion in Conferring Recognition Specificity", The Journal Of Biological Chemistry, vol. 275, No. 40, Issue of Oct. 6, pp. 31171-31177, (2000).

Carmelo Carlo-Stella et al., Molecular Pathways "Targeting TRAIL Agonistic Receptors for Cancer Therapy", Clinical Cancer Research, 13(8) pp. 2313-2317 (2007).

\* cited by examiner

NP                NP-TRAIL

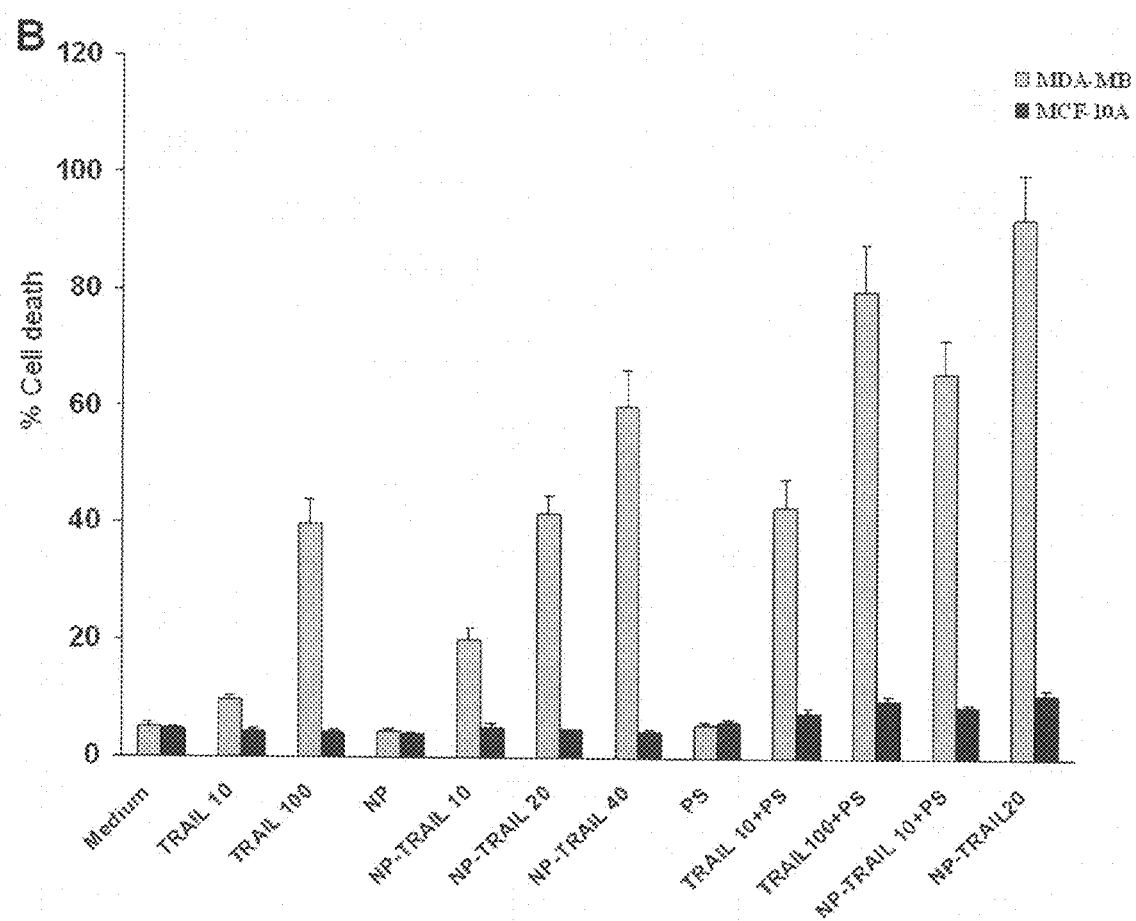

POLYMER NANOPARTICLES COATED BY MAGNETIC METAL OXIDE AND USES THEREOF

CROSS-REFERENCE TO RELATED APPLICATIONS

The present application claims the benefit of U.S. Provisional Patent Application No. 60/960,270, filed Sep. 24, 2007, the entire contents of which being herewith incorporated by reference in its entirety as if fully disclosed herein.

FIELD OF THE INVENTION

The present invention provides nanoparticles consisting of a polymer which is a metal chelating agent coated with a magnetic metal oxide, wherein at least one active agent is covalently bound to the polymer, as well as pharmaceutical compositions and uses thereof.

BACKGROUND OF THE INVENTION

Nanoparticles are spherical particles in sizes ranging from a few nanometers up to 0.1 μm. Polymeric nano-scaled particles of narrow size distribution are commonly formed by controlled precipitation methods or heterogeneous polymerization techniques, e.g., by optimal emulsion or inverse emulsion polymerization methods. Properties of solid materials undergo drastic changes when their dimensions are reduced to the nanometer size regime. It is important to keep in mind that the smaller the particles are, the larger portion of their constituent atoms is located at the surface. Nanoparticles, particularly in sizes below ca. 20 nm, predominantly exhibit surface and interface phenomena that are not observed in bulk materials, e.g., lower melting and boiling points, lower sintering temperature and reduced flow resistance.

In view of their spherical shape and high surface area, nano-scaled particles may provide neat solutions to a variety of problems in materials science, such as composite materials, catalysis, three dimensional structures and photonic uses, and can further be used in biomedical applications such as specific cell labeling and separation, cell growth, affinity chromatography, diagnostics, specific blood purification by hemoperfusion, drug delivery and controlled release (Bockstaller et al., 2003; Hergt et al., 2004; Margel et al., 1999). Each application requires polymeric nanoparticles of different optimal physical and chemical properties. The synthesis and use of numerous types of nano-scaled particles of different surface chemistry, e.g., variety of surface functional groups such as hydroxyl, carboxyl, pyridine, amide, aldehyde and phenyl chloromethyl, have already been described (Margel et al., 1999). Such nanoparticles have been designed for various industrial and medical applications, e.g., enzyme immobilization, oligonucleotide and peptide synthesis, drug delivery, specific cell labeling and separation, medical imaging, biological glues and flame retardant polymers (Bunker et al., 1994; Szymonifka and Chapman, 1995; Margel et al., 1999; WO 2004/045494; Galperin et al., 2007).

Of particular interest are particles with magnetic properties, which are usually used for separation of the particles and/or their conjugates from undesired compounds via a magnetic field. Due to their magnetic properties, these particles have several additional significant applications such as magnetic recording, magnetic sealing, electromagnetic shielding and biomedical applications. Magnetic iron oxide, i.e., magnetite and maghemite, nanoparticles are the main particles that have been investigated for biomedical applications, e.g., magnetic hyperthermia, magnetic drug targeting, magnetic cell separation and as MRI contrast agents (Lacoste et al., 1993; Green-Sadan et al., 2005; Leemputten and Horisberger, 1974; Hergt et al., 2004). Magnetic iron oxides nanoparticles are non-toxic and biodegradable, and have already been approved for clinical use as MRI contrast agents. These nanoparticles are usually prepared by adding to an aqueous solution containing stoichiometric concentrations of ferrous and ferric ions, and a polymeric stabilizer such as dextran, wherein a base, e.g., NaOH or ammonia, is added until basic pH (usually above 8.0) is reached. The obtained coated magnetic iron oxide nanoparticles are than washed by different ways, e.g., by magnetic columns or dialysis. Extensive efforts to synthesize efficient iron oxide magnetic nanoparticles have been carried out in the last several years; however, most of these nanoparticles suffer from major disadvantages such as broad size distribution that is considered to be toxic for in vivo medical applications, iron ions leaching and instability towards agglutination processes.

WO 99/062079 and corresponding EP 1088315B1 of the same Applicant, herewith incorporated by reference in their entirety as if fully disclosed herein, disclose new uniform magnetic gelatin/iron oxide composite nanoparticles, formed by controlled nucleation of iron oxide onto an iron ion chelating polymer, e.g., gelatin, dissolved in an aqueous solution, followed by stepwise growth of thin layers of iron oxide films onto the gelatin/iron oxide nuclei. These magnetic nanoparticles can be prepared in a very narrow size distribution and in sizes ranging from about 10 nm up to 100 nm.

SUMMARY OF THE INVENTION

In one aspect, the present invention provides a nanoparticle consisting of a polymer which is a metal chelating agent coated with a magnetic metal oxide, wherein at least one active agent is covalently bound to the polymer.

In another aspects, the present invention provides pharmaceutical compositions comprising nanoparticles as defined above and a pharmaceutically acceptable carrier, as well as various methods of use.

The pharmaceutical compositions of the present invention may be used, inter alia, for detection of a tumor; reducing or inhibiting the growth of a tumor or for reducing or inhibiting the growth of tumor cells left at a site in a patient from which a tumor has been surgically removed; reducing or inhibiting the growth of a tumor and monitoring the size thereof; and evaluating responsiveness of tumor cells to treatment with a candidate compound. In addition, these compositions may be used for detection of a site of inflammation and treatment of said inflammation, as well as for treatment of type 2 diabetes, obesity and anorexia.

In a further aspect, the present invention provides a nanoparticle consisting of a polymer which is a metal chelating agent coated with a magnetic metal oxide, wherein at least one agent having an anti-tumor activity selected from a peptide, a peptidomimetic, a polypeptide or a small molecule is bound to the outer surface of the magnetic metal oxide. The present invention further provides pharmaceutical compositions comprising these nanoparticles and a pharmaceutically acceptable carrier, for use in reducing or inhibiting the growth of a tumor, as well as various methods of use.

BRIEF DESCRIPTION OF THE FIGURES

The patent or application file contains at least one drawing executed in color. Copies of this patent or patent application publication with color drawings will be provided by the Office upon request and payment of the necessary fee.

FIGS. 30A-30B show the effect of TRAIL (10-100 ng/ml), gelatin/iron oxide magnetic composite nanoparticles (NP) and TRAIL-conjugated gelatin/iron oxide magnetic composite nanoparticles (NP-TRAIL, 10-40 ng bound to TRAIL/ml), both in the absence or presence of proteasome inhibitor (PS, 5 mM), on the bladder carcinoma tumor cells TSU-PR1 (30A), as well as on both the breast cancer cells MDA-MB and the normal breast cells MCF10A (30B). Cell death was determined after 24 h using LDH assay. 100% cell death was determined in Triton X-100-treated cells and data normalized.

DETAILED DESCRIPTION OF THE INVENTION

Figure 1A:
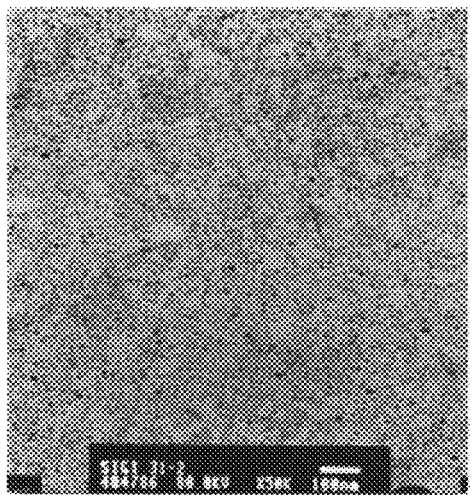
FIGS. 1A-1D show transmission electron microscopy (TEM) micrographs of gelatin/iron oxide magnetic composite nanoparticles of increased average diameter, prepared as described in Example 1, by repeating the thin magnetic coating process during the growth step 4, 5, 6 and 7 times (1A, 1B, 1C and 1D), respectively.
Figure 1B:
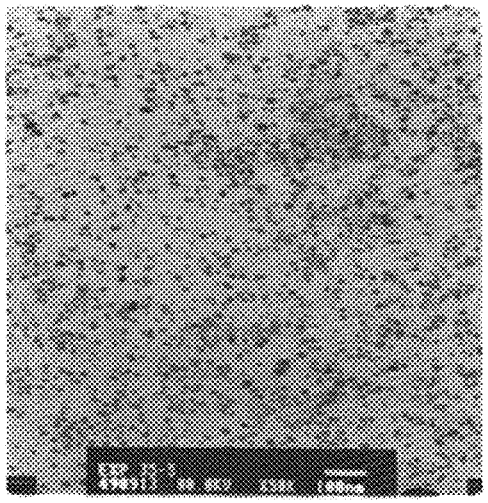
Figure 1C:
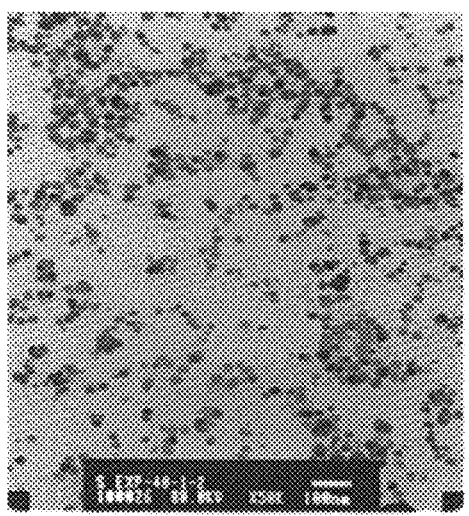
Figure 1D:
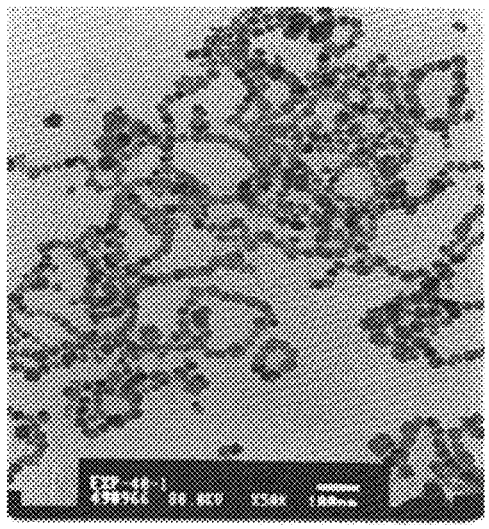

In one aspect, the present invention provides a nanoparticle consisting of a polymer which is a metal chelating agent coated with a magnetic metal oxide, wherein at least one active agent is covalently bound to the polymer.

The magnetic polymer/metal oxide composite nanoparticles of the present invention are based on the magnetic polymer/metal oxide composite nanoparticles disclosed in WO 99/062079, herewith incorporated by reference in their entirety as if fully disclosed herein; however, further comprising at least one active agent that is covalently bound to the polymer inside the nanoparticle. Such nanoparticles may be prepared by any suitable method known in the art, e.g., the process described in detail in Examples 1-3 hereinafter, namely, by controlled nucleation of a magnetic metal oxide, e.g., iron oxide, onto a metal chelating polymer, e.g., gelatin, to which at least one active agent is covalently bound, wherein said polymer is dissolved in an aqueous solution, followed by stepwise growth of thin layers of the magnetic metal oxide films onto the polymer/metal oxide nuclei. As shown in these Examples, the yield of this is almost 100%.

Examples 1-2 hereinafter describe the preparation of magnetic nanoparticles of the present invention, consisting of gelatin as a metal chelating polymer and iron oxide as a magnetic metal oxide. As shown in these examples, the magnetic nanoparticles of the present invention can be prepared in a very narrow size distribution and in sizes ranging from about 10 nm up to about 100 nm. Furthermore, these Examples particularly show the uniformity, atomic order, magnetic properties and crystalline character of the nanoparticles. The nanoparticles of the present invention are superparamagnetic, i.e., they are magnetized in the presence of a magnetic field, but no remanence is observed in the absence of a magnetic field.

Surface analysis of gelatin/iron oxide magnetic composite nanoparticles prepared as described in Examples 1-2 demonstrated the presence of gelatin both within and on the surface of the nanoparticle. As found, the surface gelatin provides additional stabilization against agglomeration to the nanoparticle, as well as functional groups such as carboxylate and primary amines through which appropriate ligands can be covalently bound.

Preferably, the size of the nanoparticles of the present invention is less than 300 nm, more preferably less than 100 nm.

According to the present invention, the metal chelating polymer used for the preparation of the nanoparticles of the present invention may be a polymer having functional groups capable of binding metal ions, particularly iron ions, selected from amino, hydroxyl, carboxylate, —SH, ether, immine, phosphate or sulfide groups. In preferred embodiments, the metal chelating polymer is selected from gelatin, polymethylenimine, chitosan or polylysine, more preferably gelatin.

In one embodiment, the magnetic metal oxide coating the aforesaid metal chelating polymer is an iron oxide or a ferrite derived from an iron oxide. The iron oxide may be a magnetite, maghemite, or a mixture thereof, and the ferrite is an oxide of the formula $(Fe,M)_3O_4$, wherein M represents a transition metal ion, preferably selected from $Zn^{2+}$, $Co^{2+}$, $Mn^{2+}$ or $Ni^{2+}$. In a preferred embodiment, the magnetic metal oxide used for the preparation of the nanoparticles of the present invention is iron oxide.

According to the present invention, the at least one active agent being covalently bound to the metal chelating polymer may be selected, without being limited to, from a fluorescent dye, a contrast agent, a peptide, a peptidomimetic, a polypeptide or a small molecule.

In one embodiment, the active agent covalently bound to the metal chelating polymer is a fluorescent dye. Examples of fluorescent dyes include, without being limited to, rhodamine or fluorescein.

In another embodiment, the active agent covalently bound to the metal chelating polymer is a contrast agent, namely a compound used to improve the visibility of internal bodily structures in either an X-ray imaging or magnetic resonance imaging (MRI). Examples of contrast agents for X-ray imaging include, without being limited to, barium sulfate-based contrast agents that are water insoluble, used in the digestive tract only either swallowed or administered as an enema, and iodine-based water soluble contrast agents, which can be used almost anywhere in the body, in particular, intravenously as well as intraarterially, intrathecally (the spine) and intraabdominally. Commonly used iodinated contrast agents are diatrizoate (Hypaque 50), metrizoate (Isopaque Coronar 370), ioxaglate (Hexabrix), iopamidol (Isovue 370), iohexyl (Omnipaque 350), ioxilan (Oxilan), iopromide and iodixanol (Visipaque 320).

In a further embodiment, the active agent covalently bound to the metal chelating polymer is a peptide or a peptidomimetic.

The arginine-glycine-aspartic acid (Arg-Gly-Asp; RGD) motif of extracellular matrix components such as fibronectin and vitronectin binds to integrins, and integrin-mediated adhesion leads to intracellular signaling events that regulate cell survival, proliferation and migration. Data obtained by phage display methods screening for RGD-containing peptides have shown their selective binding to endothelial lining of tumor blood vessels. RGD peptides also retard signal transmission, affect cell migration and induce tumor cell regression or apoptosis. By binding to integrin of either endothelial or tumor cells, RGD peptides are capable of modulating in vivo cell traffic by inhibition of tumor cell-extracellular matrix and tumor cell-endothelial cell attachments, which are obligatory for metastatic processes. Several studies have indicated that RGD-containing compounds can interfere with tumor cell metastatic processes in vitro and in vivo. Peptides that are specific for individual integrins are of considerable interest and of possible medical significance. The $\alpha_v\beta_3$ integrin was the first integrin shown to be associated with tumor angiogenesis, and RGD peptides that specifically block the $\alpha_v\beta_3$ integrin show promise as inhibitors of tumor and retinal angiogenesis, of osteoporosis and in targeting drugs to tumor vasculature. Consequently, a great amount of work was invested in designing and producing integrin-binding peptides and peptidomimetics.

In one preferred embodiment, the peptide or peptidomimetic is thus a cyclic RGD (cRGD) peptide or peptidomimetic, or an acyclic RGD-containing peptide or peptidomimetic. In a more preferred embodiment, the cRGD peptide is the cRGD peptide of the sequence cyclo (Arg-Gly-Asp-D-Phe-Lys (SEQ ID NO: 1).

In yet a further embodiment, the active agent covalently bound to the metal chelating polymer is a polypeptide.

Tumor necrosis factor-related apoptosis-inducing ligand (TRAIL, also referred to as Apo-2 ligand, Apo-2L or TRAIL/Apo2L) is a member of the tumor necrosis factor (TNF) family of cytokines, capable of initiating apoptosis through engagement of its death receptors. Additional members of this family are, e.g., TNFα (also referred to as TNF), TNFβ, TL1A (a TNF-like ligand), lymphotoxix-β (LTβ), CD30 ligand, CD27 ligand, CD40 ligand, OX-40 ligand, 4-1BB ligand, Apo-1 ligand (also referred as Fas ligand or CD95 ligand), Apo-3 ligand (also referred to as RANK ligand, ODF or TRANCE) and TALL-1 (also referred to as BlyS, BAFF or THANK) (WO 2004/001009; Wang and El-Deiry, 2003).

TRAIL is a type II transmembrane protein initially identified and cloned based on the sequence homology of its extracellular domain with CD95L (28% identical) and TNF (23% identical). The native sequence of human TRAIL polypeptide is 281 amino acids long; however, some cells can produce a natural soluble form of the polypeptide, through enzymatic cleavage of the polypeptide extracellular region. Like most other TNF family members, TRAIL forms homotrimers that bind the receptor molecules, each at the interface between two of its subunits. Indeed, TRAIL like most of the TNF ligand family occurs in both a membrane-bound and a soluble form, which can possess different bioactivity. Four members of the TNF family, i.e., Fas ligand, TNFα, TL1A and TRAIL, stand out because of their ability to induce apoptosis. Unlike other TNF family members, soluble TRAIL (sTRAIL) has a unique structural feature in which the cysteine residues together coordinate a Zn atom, which is essential for trimer stability and optimal biological activity. Functional studies showed that TRAIL has a potent ability to induce apoptosis, in vitro, in a variety of tumor cell lines including colon, lung, breast, prostate, bladder, kidney, ovarian and brain tumors, as well as melanoma, leukemia and multiple myeloma, but not in most normal cells, highlighting its potential therapeutic application in cancer treatment (WO 2004/001009; Wang and El-Deiry, 2003; Ashkenazi et al., 1999; Carlo-Stella et al., 2007; Smyth et al., 2003). There are only very few agents that are truly cancer cell-specific in term of efficacy or cell death induction as TRAIL. In contrast to other TNF family members, whose expressions are tightly regulated and are often only transiently expressed on activated cells, TRAIL mRNA is constitutively expressed in a wide range of tissues. Although the main biological function of TRAIL seems to be the induction of apoptosis, the complete physiological role of this ligand is not yet fully understood. It appears likely that TRAIL expression on liver natural killer (NK) cells is regulated by IFNγ secreted from NK cells in an autocrine manner, since a large portion of NK cells constitutively produce both TRAIL and IFNγ in wild-type and T-cell-deficient mice. Mouse gene knockout studies indicated that TRAIL has an important role in antitumor surveillance by immune cells, and that it mediates thymocyte apoptosis and it is important in the induction of autoimmune diseases.

TRAIL induces apoptosis through interacting with its receptors. So far, four homologous human receptors for TRAIL have been identified, including DR4, KILLER/DR5, DcR1 (Trail-R3 TRID) and DcR2 (TRAIL-R4), as well as a fifth soluble receptor called osteoprotegerin (OPG), initially identified as a RANKL/OPGL receptor. Both DR4 and DR5 contain a conserved death domain (DD) motif and can signal apoptosis. The other three receptors appear to act as "decoys" for their ability to inhibit TRAIL-induced apoptosis when over expressed. Decoy receptor 1 (DcR1) and DcR2 have close homology to the extra-cellular domains of DR4 and DR5. DcR2 has a truncated, nonfunctional cytoplasmic DD, while DcR1 lacks a cytosolic region and is anchored to the plasma membrane though a glycophospholipid moiety. The physiological relevance of OPG as a receptor for TRAIL is unclear because the affinity for this ligand at physiological temperatures is very low. On possible explanation for the selective antitumoral activity of TRAIL is that the decoy receptors are preferentially expressed in normal cells and interfere with TRAIL action (WO 2004/001009; Wang and El-Deiry, 2003; Carlo-Stella, 2007; Shah et al., 2003). Another possible explanation is that most tumor cell lines express the agonist TRAIL receptors but no or undetectable levels of the antagonist receptors, whereas normal cells have been found to express antagonist TRAIL receptors, and therefore, TRAIL may allow selective killing of tumor cells only (Wei et al., 2006).

Despite early promising results, recent studies have identified several TRAIL-resistant cancer cells in various tumors. Resistance of cancer cells to TRAIL appears to occur through the modulation of various molecular targets, which may include differential expression of death receptors. Based on molecular analysis of death-receptor signaling pathways several new approaches have been developed to increase the efficacy of TRAIL, including the administration of conventional cancer drugs or irradiation, in combination with TRAIL (Shankar and Srivastava, 2004; Smyth et al., 2003).

Thus, in one preferred embodiment, the polypeptide is a cytokine, for example, tumor necrosis factor (TNF)-α, TNF-β; a TNF-related cytokine or an interleukin (IL). Non-limiting examples of TNF-related cytokines include TNF-related apoptosis-inducing ligand (TRAIL), TALL-1, the TNF-like ligand TL1A, lymphotoxin-beta (LT-β), CD30 ligands, CD27 ligands, CD40 ligands, OX40 ligands, 4-1BB ligands, Apo-1 ligands and Apo-3 ligands, with TRAIL being preferred. In a most preferred embodiment, the cytokine is TRAIL. Non-limiting examples of interleukins include any interleukin that has an anti-tumor activity, with IL-12, IL-23 and IL-27 being preferred.

In another embodiment, the polypeptide is an enzyme.

In a further embodiment, the polypeptide is an antibody such as avastin or remicade. Avastin is a monoclonal antibody against vascular endothelial grow factor (VEGF), which is used in the treatment of cancer for inhibiting the growth of tumors by blocking the formation of new blood vessels. Remicade is a monoclonal antibody used for treatment of autoimmune disorders by binding to TNFα, one of the key cytokines that triggers and sustains the inflammation response, and preventing it from binding to TNFα receptors.

In still a further embodiment, the polypeptide is a hormone, i.e., a polypeptide hormone such as insulin, obestatin or ghrelin.

In another embodiment, the active agent covalently bound to the metal chelating polymer is a small molecule.

In one preferred embodiment, the small molecule is an anthracycline chemotherapeutic agent. The anthracycline chemotherapeutic agent may be any chemotherapeutic agent of the anthracycline family including daunorubicin (also known as adriamycin), doxorubicin, epirubicin, idarubicin and mitoxantrone. In a more preferred embodiment, the anthracycline chemotherapeutic agent is doxorubicin, which is a quinine-containing anthracycline and is the most widely prescribed and effective chemotherapeutic agent utilized in oncology. Doxorubicin is indicated in a wide range of human malignancies, including tumors of the bladder, stomach, ovary, lung and thyroid, and is one of the most active agents available for treatment of breast cancer and other indications, including acute lymphoblastic and myelogenous leukemias, Hodgkin's and non-Hodgkin's lymphomas, Ewing's and osteogenic bone tumors, soft tissue sarcomas, and pediatric cancers such as neuroblastoma and Wilms' tumors.

In another preferred embodiment, the small molecule is an antifolate drug, i.e., a drug which impairs the function of folic acid. A well known and a preferred example of an antifolate drug is methotrexate, which is a folic acid analog that inhibits the enzyme dihydrofolate reductase, and thus prevents the formation of tetrahydrofolate that is essential for purine and pyrimidine synthesis, and consequently leads to inhibited production of DNA, RNA and proteins. Other examples of antifolate agents include trimethoprim, pyrimethamine and pemetrexed. As antifolates interfere with metabolism of nucleotides, their action specifically targets the fast-dividing cells.

In a further preferred embodiment, the small molecule is an antibiotic.

In still another preferred embodiment, the small molecule is an amine-derived hormone, i.e., a derivative of the amino acids tyrosine and tryptophan. Non-limiting examples of amine-derived hormones include catecholamines, e.g., epinephrine, norepinephrine and dopamine, and thyroxine.

In yet another preferred embodiment, the small molecule is a lipid- or phospholipid-derived hormone, i.e., a hormone derive from lipids such as linoleic acid and arachidonic acid and phospholipids. The main classes of lipid- and phospholipid-derived hormones are the steroid hormones derived from cholesterol, e.g., testosterone and cortisol, and the eicosanoids, i.e., prostaglandins.

In still a further preferred embodiment, the small molecule is an anti-inflammatory agent.

The anti-inflammatory agent may be selected from a corticosteroid, the alkaloid colchicine that is the standard treatment for gout, or non-steroidal anti-inflammatory drugs (NSAIDs) such as, but not limited to, aspirin, choline and magnesium salicylates, choline salicylate, celecoxib, diclofenac, diflunisal, etodolac, fenoprofen calcium, flurbiprofen, ibuprofen, indomethacin, ketoprofen, magnesium salicylate, meclofenamate sodium mefenamic acid, meloxicam, nabumetone, naproxen, oxaprozin, piroxicam, rofecoxib, salsalate, sodium salicylate, sulindac, tolmetin sodium and valdecoxib.

In view of all the aforesaid, in one preferred embodiment, the metal chelating polymer is gelatin, the metal oxide is iron oxide, and the agent covalently bound to the gelatin is selected from (i) a fluorescent dye, preferably rhodamine or fluorescein; (ii) a TNF or a TNF-related cytokine, preferably TRAIL; (iii) an anthracycline chemotherapeutic agent, preferably doxorubicin; (iv) an antifolate drug, preferably methotrexate; or (v) a combination thereof. In a more preferred embodiment, said at least one agent covalently bound to the gelatin is a fluorescent dye or TRAIL.

According to the present invention, the nanoparticles defined above may further comprise at least one active agent physically or covalently bound to the outer surface of the magnetic metal oxide, wherein said at least one active agent is the same or different from the at least one active agent covalently bound to the polymer.

In one embodiment, said active agent is covalently bound to the outer surface of the magnetic metal oxide.

As demonstrated in Example 4 hereinafter, various techniques were established to stabilize and covalently bind external functional groups to these magnetic nanoparticles, by coating them with a variety of polymers, e.g., polysaccharides, proteins and polyethyleneglycols. The functional groups of these coatings were then used for covalent binding of different reagents, e.g., proteins, enzymes and drugs for biomedical applications.

Thus, in one embodiment, the active agent covalently bound to the outer surface of the magnetic metal oxide is bound, in fact, via a molecule containing a functional group attached to the magnetic metal oxide surface. In certain embodiments, this molecules comprise a polymer selected from a polysaccharide, more preferably chitosan, a protein, more preferably gelatin or albumin, a peptide, or a polyamines.

In another embodiment, the active agent covalently bound to the outer surface of the magnetic metal oxide is bound, in fact, via an activating ligand attached to the magnetic metal oxide outer surface. In preferred embodiments, the activating ligand is acryloyl chloride, divinyl sulfone (DVS), dicarbonyl imidazole, ethylene glycolbis(sulfosuccinimidylsuccinate) or m-maleimidobenzoic acid N-hydroxysulfosuccinimide ester. In a more preferred embodiment, the activating ligand is DVS.

As stated above, in certain cases the activating ligands may further be attached to the polymer extending outside the metal oxide coating.

As shown in Example 5, the active agent may also be physically bound to the outer surface of the magnetic metal oxide. This physical binding is based on non-covalent interactions, e.g., hydrophobic bonds, ionic interactions and hydrogen bonds, between the active agent(s) and the outer surface of the magnetic metal oxide.

Thus, in another embodiment, the active agent(s) of (b) is physically bound to the outer surface of the magnetic metal oxide.

According to the present invention, the at least one active agent being bound to the outer surface of the magnetic metal oxide may be selected, without being limited to, a peptide, a peptidomimetic, a polypeptide or a small molecule, as defined above for the active agent covalently bound to the polymer. In one embodiment, said peptide or peptidomimetic is a cyclic RGD (cRGD) peptide or peptidomimetic, preferably the cRGD peptide of SEQ ID NO: 1, or an acyclic RGD-containing peptide or peptidomimetic; said polypeptide is a cytokine, an enzyme, an antibody, preferably avastin or remicade, or a hormone, preferably insulin, obestatin or ghrelin; said cytokine is selected from tumor necrosis factor (TNF)-α, TNF-β, a TNF-related cytokine selected from TNF-related apoptosis-inducing ligand (TRAIL), TALL-1, the TNF-like ligand TL1A, lymphotoxin-beta (LT-β), a CD30 ligand, a CD27 ligand, a CD40 ligand, an OX40 ligand, a 4-1BB ligand, an Apo-1 ligand, or an Apo-3 ligand, preferably TRAIL, or an interleukin (IL), preferably IL having an anti-tumor activity, more preferably IL-12, IL-23 or IL-27; and said small molecule is selected from an antifolate drug such as methotrexate, an antibiotic, an amine-derived hormone, a lipid- or phospholipid-derived hormone, an anti-inflammatory agent, or an anthracycline chemotherapeutic agent selected from daunorubicin, doxorubicin, epirubicin, idarubicin or mitoxantrone, preferably doxorubicin.

The concentrations of the active agent(s) bound, either covalently or physically, to the surface of the magnetic metal oxide may be controlled by changing binding parameters, e.g., active agent(s) concentration in the process.

In one preferred embodiment, the present invention provides nanoparticles as defined above, wherein said polymer is gelatin, said magnetic metal oxide is iron oxide, said at least one active agent covalently bound to the polymer is selected from (i) a fluorescent dye, preferably rhodamine or fluorescein; (ii) a TNF or a TNF-related cytokine, preferably TRAIL; (iii) an anthracycline chemotherapeutic agent, preferably doxorubicin; (iv) an antifolate drug, preferably methotrexate; or (v) a combination thereof, and said at least one active agent bound to the outer surface of the magnetic metal oxide is selected from: (vi) a TNF or a TNF-related cytokine, preferably TRAIL; (vii) a cRGD peptide, preferably the cRGD peptide of SEQ ID NO: 1; (viii) an interleukin having an anti-tumor activity, preferably IL-12; or (ix) a combination thereof. In a more preferred embodiment, said at least one active agent covalently bound to the polymer is a fluorescent dye or TRAIL, and said at least one active agent bound to the outer surface of the magnetic metal oxide is TRAIL.

In another aspect, the present invention provides a pharmaceutical composition comprising magnetic polymer/metal oxide composite nanoparticles as defined above and a pharmaceutically acceptable carrier.

The pharmaceutical composition of the present invention may be used for various biological, medical and therapeutical applications.

In one embodiment, the pharmaceutical composition of the present application is used for diagnostics, drug stabilization, drug delivery and controlled release of drugs.

In one embodiment, the pharmaceutical composition of the present invention comprises magnetic polymer/metal oxide composite nanoparticles as defined above, preferably gelatin/iron oxide composite nanoparticles, wherein the at least one active agent covalently bound to the polymer is a fluorescent dye. This pharmaceutical composition may be used for tumor detection.

In one embodiment, the pharmaceutical composition of the present invention comprises magnetic polymer/metal oxide composite nanoparticles as defined above, preferably gelatin/iron oxide composite nanoparticles, wherein the at least one active agent covalently bound to the polymer is a contrast agent. This pharmaceutical composition may be used for X-ray imaging or magnetic resonance imaging (MRI). The present invention thus relates to a method for X-ray imaging or magnetic resonance imaging (MRI) comprising administering to an individual in need said pharmaceutical composition.

In a preferred embodiment, this composition may further comprise a molecule capable of binding a tumor specific cellular marker bound to the outer surface of the magnetic metal oxide. This composition may be used for tumor detection. The present invention thus relates to a method for detection of a tumor comprising administering to an individual in need the pharmaceutical composition defined above.

The term "molecule capable of binding a tumor specific cellular marker" as used herein refers to antibodies or fragments thereof directed to tumor associated antigens; receptors or fragments thereof specific for tumor associated ligands; or ligands of tumor associated receptors.

In a further embodiment, the pharmaceutical composition of the present invention comprises magnetic polymer/metal oxide composite nanoparticles as defined above, preferably gelatin/iron oxide composite nanoparticles, wherein the at least one active agent covalently bound to the polymer and said at least one active agent bound to the outer surface of the magnetic metal oxide, the same or different, are selected from TNF-α, TNF-β, a TNF-related cytokine selected from TNF-related apoptosis-inducing ligand (TRAIL), TALL-1, the TNF-like ligand TL1A, lymphotoxin-beta (LT-β), a CD30 ligand, a CD27 ligand, a CD40 ligand, an OX40 ligand, a 4-1BB ligand, an Apo-1 ligand, or an Apo-3 ligand, an interleukin having an anti-tumor activity selected from IL-12, IL-23 or IL-27, a cRGD peptide, preferably the cRGD peptide of SEQ ID NO:1, a cRGD peptidomimetic, an RGD containing peptide or peptidomimetic, an antibody, preferably avastin, an anthracycline chemotherapeutic agent selected from daunorubicin, doxorubicin, epirubicin, idarubicin or mitoxantrone, an antifolate drug, or a combination thereof. In a preferred embodiment, said at least one active agent covalently bound to the polymer is selected from TRAIL, doxorubicin, methotrexate or a combination thereof, and said at least one active agent bound to the outer surface of the magnetic metal oxide is selected from TRAIL, the cRGD peptide of SEQ ID NO: 1, IL-12, or a combination thereof. This pharmaceutical composition may be used for reducing or inhibiting the growth of a tumor, or for reducing or inhibiting the growth of tumor cells remaining at a site in a patient from which a tumor has been surgically removed. The present invention thus further relates to a method for reducing or inhibiting the growth of a tumor or for reducing or inhibiting the growth of tumor cells left at a site in a patient from which a tumor has been surgically removed, comprising administering to said patient said pharmaceutical composition.

In still a further embodiment, the pharmaceutical composition of the present invention comprises magnetic polymer/metal oxide composite nanoparticles as defined above, preferably gelatin/iron oxide composite nanoparticles, wherein the at least one active agent covalently bound to the polymer is a fluorescent dye or a contrast agent, and said at least one active agent bound to the outer surface of the magnetic metal oxide is selected from TNF-α, TNF-β, a TNF-related cytokine selected from TNF-related apoptosis-inducing ligand (TRAIL), TALL-1, the TNF-like ligand TL1A, lymphotoxin-beta (LT-β), a CD30 ligand, a CD27 ligand, a CD40 ligand, an OX40 ligand, a 4-1BB ligand, an Apo-1 ligand, or an Apo-3 ligand, an interleukin having an anti-tumor activity selected from IL-12, IL-23 or IL-27, a cRGD peptide, preferably the cRGD peptide of SEQ ID NO: 1, a cRGD peptidomimetic, an RGD containing peptide or peptidomimetic, an antibody, preferably avastin, an anthracycline chemotherapeutic agent selected from daunorubicin, doxorubicin, epirubicin, idarubicin or mitoxantrone, an antifolate drug, or a combination thereof. In a preferred embodiment, said at least one active agent bound to the outer surface of the magnetic metal oxide is selected from TRAIL, the cRGD peptide of SEQ ID NO: 1, IL-12, or a combination thereof. This pharmaceutical composition may be used for reducing or inhibiting the growth of a tumor and monitoring the size thereof. The present invention thus further relates to a method for reducing or inhibiting the growth of a tumor and monitoring the size thereof in a patient comprising administering to said patient said pharmaceutical composition.

The term "tumor" as used herein refers to any tumor such as, without being limited to, brain tumors, preferably glioma, colon cancer, lung cancer, breast cancer, prostate cancer, bladder cancer, kidney cancer, ovarian cancer, melanoma, leukemia or multiple myeloma, preferably glioma, and metastases thereof. In a preferred embodiment, the tumor is glioma.

Brain tumors, in particular, malignant gliomas, belong to the most aggressive human cancers. Patients with malignant glioma have a poor prognosis because these brain tumors respond poorly to radiation or chemotherapy, the conventional treatments of cancer (Wei et al., 2006). Features responsible for the aggressive character of glioma include rapid proliferation, diffuse growth and invasion into distant brain areas in addition to extensive cerebral edema and high levels of angiogenesis. Patients with malignant gliomas posses a median survival of less than one year, wherein there are only occasional long-term survivors. The difficulty in differentiating tumor and normal brain tissue, and the unusual ability of gliomas to infiltrate the brain pose a serious challenge in glioma therapy and diagnosis (Giese et al., 2003), and it is currently not expected that further advances in neurosurgery, radiation therapy or chemotherapy will significantly improve the prognosis of these patients (Desjardins et al., 2005).

Furthermore, in modern clinical neurooncology, histopathological diagnosis affects therapeutic decisions and prognostic estimation more than any other parameter. Unfortunately, the extensive heterogeneity of astrocytic tumors has made their pathological classification rather difficult (Sanson et al., 2004). Currently there are no specific markers for glioblastomas and the diagnosis of these patients is determined by histological evaluation of tumor samples. More-over, no markers are available for predicting the progression of low-grade astrocytomas to glioblastomas. Thus, the identification of glioma-specific markers can assist in the diagnosis of brain tumors and in the prediction of the prognosis and tumor progression of low-grade astrocytomas.

Malignant gliomas, including the anaplastic astrocytoma and glioblastoma multiform, are the most common primary brain tumors. Current treatment options include surgery, radiation therapy and chemotherapy; however, prognosis remains extremely poor and the development of alternative therapeutic approaches is thus highly desirable. Gene therapy has been considered as an innovative therapeutic approach for malignant gliomas, and in the last decade there has been a great interest in the development of delivery systems that will allow the expression of exogenous genes in the central nervous system. For this purpose, plasmid or vector encoding tumor necrosis factor-related apoptosis-inducing ligand (TRAIL), incorporated into cationic albumin nanoparticles, liposomes and replication-deficient herpes simplex virus (HSV), have been developed (Shah et al., 2003; Van Meir and Bellail, 2004; Carlo-Stella et al., 2007; Wei Lu et al., 2006; Zhang et al., 2002). However, no convincing clinical trial has emerged, providing objective proof of the superiority of gene therapy strategy as compared to conventional treatment. An alternative approach to gene therapy includes the direct delivery of TRAIL into the tumors. This approach, however, presents a challenge due to the limited stability of the TRAIL as well as its low bioavailability, inefficiency in crossing cell membranes and poor in vivo metabolic stability (Denicourt and Dowdy, 2004; Shir and Levitzki, 2001; Shah et al., 2003; WO 2004/045494).

Thus, in a preferred embodiment, the tumor is glioma.

The pharmaceutical composition of the present invention, when aimed for reducing or inhibiting the growth of a tumor, either with or without monitoring the size thereof, or for reducing or inhibiting the growth of tumor cells left at a site in a patient from which a tumor has been surgically removed, may be used in combination with radiotherapy. In view of that, the various methods defined above for (i) reducing or inhibiting the growth of a tumor; (ii) reducing or inhibiting the growth of tumor cells left at a site in a patient from which a tumor has been surgically removed; or (iii) reducing or inhibiting the growth of a tumor and monitoring the size thereof, may be performed in combination with radiotherapy.

Since it is known that iron oxide is attracted to sites of inflammation, in yet a further embodiment, the pharmaceutical composition of the present invention comprises magnetic polymer/metal oxide composite nanoparticles as defined above, wherein said magnetic metal oxide is iron oxide, said at least one active agent covalently bound to the polymer is a fluorescent dye or a contrast agent and said at least one active agent bound to the outer surface of the magnetic metal oxide is an anti-inflammatory agent. This pharmaceutical composition may be used for detection of a site of inflammation and treatment of said inflammation in an individual. The present invention thus relates to a method for detection of a site of inflammation and treatment of said inflammation comprising administering to an individual in need said pharmaceutical composition.

In still another embodiment, the pharmaceutical composition of the present invention comprises magnetic polymer/metal oxide composite nanoparticles as defined above, preferably gelatin/iron oxide composite nanoparticles, wherein said at least one active agent covalently bound to the polymer and said at least one active agent bound to the outer surface of the magnetic metal oxide, each independently, is insulin. This pharmaceutical composition may be used for treatment of type 2 diabetes. The present invention thus relates to a method for treatment of type 2 diabetes comprising administering to an individual in need said pharmaceutical composition.

In yet another embodiment, the pharmaceutical composition of the present invention comprises magnetic polymer/metal oxide composite nanoparticles as defined above, preferably gelatin/iron oxide composite nanoparticles, wherein said at least one active agent covalently bound to the polymer and said at least one active agent bound to the outer surface of the magnetic metal oxide, each independently, is obestatin. This pharmaceutical composition may be used for treatment of obesity. The present invention thus relates to a method for treatment of obesity comprising administering to an individual in need said pharmaceutical composition.

In a further embodiment, the pharmaceutical composition of the present invention comprises magnetic polymer/metal oxide composite nanoparticles as defined above, preferably gelatin/iron oxide composite nanoparticles, wherein said at least one active agent covalently bound to the polymer and said at least one active agent bound to the outer surface of the magnetic metal oxide, each independently, is ghrelin. This pharmaceutical composition may be used for treatment of anorexia. The present invention thus relates to a method for treatment of anorexia comprising administering to an individual in need said pharmaceutical composition.

In a further aspect, the present invention relates to a method for evaluating responsiveness of tumor cells to treatment with a candidate compound, which comprises contacting cells from a biopsy taken from said tumor with magnetic polymer/metal oxide composite nanoparticles as defined above, preferably gelatin/iron oxide composite nanoparticles, and monitoring the viability of the tumor cells, wherein the active agent bound to the outer surface of the magnetic metal oxide in the nanoparticles is the candidate compound to be evaluated and is selected from TNF-$\alpha$, TNF-$\beta$, a TNF-related cytokine selected from TNF-related apoptosis-inducing ligand (TRAIL), TALL-1, the TNF-like ligand TL1A, lymphotoxin-beta (LT-$\beta$), a CD30 ligand, a CD27 ligand, a CD40 ligand, an OX40 ligand, a 4-1BB ligand, an Apo-1 ligand, or an Apo-3 ligand, an interleukin having an anti-tumor activity selected from IL-12, IL-23 or IL-27, a cRGD peptide, preferably the cRGD peptide of SEQ ID NO: 1, a cRGD peptidomimetic, an RGD containing peptide or peptidomimetic, an antibody, preferably avastin, an anthracycline chemotherapeutic agent selected from daunorubicin, doxorubicin, epirubicin, idarubicin or mitoxantrone, an antifolate drug, or a combination thereof, and the nanoparticles comprise a fluorescent dye or a contrast agent covalently bound to the polymer.

In another aspect, the present invention provides a nanoparticle consisting of a polymer which is a metal chelating agent coated with a magnetic metal oxide, wherein at least one agent having an anti-tumor activity selected from a peptide, a peptidomimetic, a polypeptide or a small molecule is bound to the outer surface of the magnetic metal oxide.

The various definitions with respect to the size of the nanoparticles having an anti-tumor agent bound exclusively to their outer surface, as well as to the metal chelating polymer and the magnetic metal oxide are identical to those defined with respect to the magnetic nanoparticles defined above, in which at least one active agent is covalently bound to the polymer. Furthermore, and as defined with respect to the magnetic nanoparticles, the agent having an anti-tumor activity may be either covalently or physically bound to the outer surface of the magnetic metal oxide.

As defined above, the agent having anti-tumor activity may be a peptide, a peptidomimetic, a polypeptide or a small molecule.

In one embodiment, the agent having anti-tumor activity is a peptide or peptidomimetic such as a cRGD peptide or peptidomimetic, or an acyclic RGD-containing peptide or peptidomimetic. In a preferred embodiment, the cRGD peptide is the cRGD peptide of SEQ ID NO: 1.

In a further embodiment, the agent having anti-tumor activity is a polypeptide such as a cytokine, for example, TNF-α, TNF-β; a TNF-related cytokine or an interleukin. Non-limiting examples of TNF-related cytokines include TNF-related apoptosis-inducing ligand (TRAIL), TALL-1, the TNF-like ligand TL1A, lymphotoxin-beta (LT-β), CD30 ligands, CD27 ligands, CD40 ligands, OX40 ligands, 4-1BB ligands, Apo-1 ligands, and Apo-3 ligands. In preferred embodiment, the cytokine is TRAIL, IL-12, IL-23 or IL-27, more preferably TRAIL.

In yet another embodiment, the agent having anti-tumor activity is a small molecule. Non-limiting examples of small molecules include anthracycline chemotherapeutic agents and antifolate drugs, as defined above, preferably doxorubicin and methotrexate, respectively.

In one embodiment, the present invention provides nanoparticles having an anti-tumor agent bound exclusively to their outer surface, wherein said peptide or peptidomimetic is a cRGD peptide or peptidomimetic, preferably the cRGD peptide of SEQ ID NO: 1, or an acyclic RGD-containing peptide or peptidomimetic; said polypeptide is a cytokine selected from TNF-α, TNF-β, a TNF-related cytokine selected from TNF-related apoptosis-inducing ligand (TRAIL), TNF-α, TNF-β, TALL-1, the TNF-like ligand TL1A, lymphotoxin-beta (LT-β), a CD30 ligand, a CD27 ligand, a CD40 ligand, an OX40 ligand, a 4-1BB ligand, an Apo-1 ligand, or an Apo-3 ligand, preferably TRAIL, an interleukin (IL), preferably IL-12, IL-23 or IL-27, or an antibody, preferably avastin; said small molecule is an antifolate drug selected from methotrexate or an anthracycline chemotherapeutic agent selected from daunorubicin, doxorubicin, epirubicin, idarubicin and mitoxantrone, preferably doxorubicin; or a combination thereof. In a preferred embodiment, said polymer is gelatin, said magnetic metal oxide is iron oxide, and said at least one agent having an anti-tumor activity is a TNF or a TNF-related cytokine, an anthracycline chemotherapeutic agent, an antifolate drug or a combination thereof. In a most preferred embodiment, said at least one agent having anti-tumor activity is TRAIL.

In still another aspect, the present invention provides a pharmaceutical composition comprising nanoparticles having an anti-tumor agent bound exclusively to their outer surface as defined above and a pharmaceutically acceptable carrier, for use in reducing or inhibiting the growth of a tumor.

In a preferred embodiment, this pharmaceutical composition comprising nanoparticles having an anti-tumor agent bound exclusively to their outer surface, wherein the at least one agent having an anti-tumor activity is TRAIL, the cRGD peptide of SEQ ID NO: 1, IL-12, doxorubicin, methotrexate or a combination thereof.

The nanoparticles having an anti-tumor agent bound exclusively to their outer surface, as defined above, may be used for reducing or inhibiting the growth of a tumor or for reducing or inhibiting the growth of tumor cells left at a site in a patient from which a tumor has been surgically removed. The present invention thus further relates to a method for reducing or inhibiting the growth of a tumor or for reducing or inhibiting the growth of tumor cells left at a site in a patient from which a tumor has been surgically removed, comprising administering to said patient the aforesaid pharmaceutical composition. As explained above, these nanoparticles may be used in combination with radiotherapy. Therefore, this method may be performed in combination with radiotherapy.

In yet another aspect, the present invention relates to a method for evaluating responsiveness of tumor cells to treatment with a candidate compound, which comprises contacting cells from a biopsy taken from said tumor with nanoparticles having an anti-tumor agent bound exclusively to their outer surface, as defined above, preferably gelatin/iron oxide composite nanoparticles having an anti-tumor agent bound exclusively to their outer surface, and monitoring the viability of the tumor cells, wherein the antitumor agent bound to the outer surface of the magnetic metal oxide of the nanoparticles is the candidate compound to be evaluated.

The pharmaceutical composition provided by the present invention may be prepared by conventional techniques, e.g., as described in Remington: The Science and Practice of Pharmacy, 19th Ed., 1995. The composition may be in solid, semisolid or liquid form and may further include pharmaceutically acceptable fillers, carriers or diluents, and other inert ingredients and excipients. Furthermore, the pharmaceutical composition can be designed for a slow release of the nanoparticles. The composition can be administered by any suitable route, e.g. intravenously, orally, parenterally, rectally, transdermally or topically. The dosage will depend on the state of the patient, and will be determined as deemed appropriate by the practitioner.

The route of administration may be any route which effectively transports the active compound to the appropriate or desired site of action, the intravenous route being preferred. If a solid carrier is used for oral administration, the preparation may be tabletted, placed in a hard gelatin capsule in powder or pellet form or it can be in the form of a lozenge. If a liquid carrier is used, the preparation may be in the form of a syrup, emulsion or soft gelatin capsule. Tablets, dragees or capsules having talc and/or a carbohydrate carrier or binder or the like are particularly suitable for oral application. Preferable carriers for tablets, dragees or capsules include lactose, corn starch and/or potato starch.

As stated above, malignant gliomas are the most common primary intracranial tumors in patients. The prognosis of these tumors is poor because they poorly respond to radiation or chemotherapy. The difficulty in differentiating tumor and normal brain tissue, and the unusual ability of gliomas to infiltrate the brain pose a serious challenge in glioma therapy and diagnosis.

TRAIL is a transmembrane protein initially expressed at the cell membrane and subsequently derived by proteolytic processing. Soluble TRAIL (sTRAIL) can induce apoptosis in tumor cells of diverse origins while sparing most normal cells. However, while most previous studies have been performed in cell culture, the delivery and efficiency of sTRAIL in vivo is significantly less established and successful. The major hindrance for in vivo sTRAIL treatment is due to its short half-life due to proteolytic cleavage, which therefore requires excess amount of sTRAIL. In vivo sTRAIL treatment is particularly inefficient for glioma tumors due to difficulties in the administration of TRAIL to the brain and to the relative insensitivity of gliomas to TRAIL in vivo.

Examples 6-8 hereinafter describe in detail various in vitro and in vivo experiments conducted with gelatin/iron oxide magnetic composite nanoparticles of the present invention, both when at least one active agent was covalently bound to the polymer inside the nanoparticles and, optionally, the same or different active agent was bound to the outer surface of the magnetic metal oxide; as well as when no active agent was covalently bound to the polymer.

As shown in these Examples, the conjugation of TRAIL both to fluorescent and to non-fluorescent gelatin/iron oxide composite nanoparticles significantly stabilized the sTRAIL, minimizing enzymatic degradation of the sTRAIL and thereby decreasing the amount of sTRAIL essential for apoptosis of tumor cells. This approach allows the selective delivery of sTRAIL to tumor cells for efficient apoptosis. Furthermore, the sTRAIL-conjugated nanoparticles selectively tracked infiltrating tumor cells, exerted cytotoxic effects in vivo, and significantly increased the survival of tumor-bearing animals. Tumor cells which were resistant to the cytotoxic effect of the sTRAIL-conjugated nanoparticles were sensitized by using a combined treatment of low-level of γ-irradiation followed by treatment with the sTRAIL-conjugated nanoparticles. Alternatively, these cells were efficiently treated with nanoparticles to which more than one active agent was conjugated. The active agents used for this purpose were sTRAIL, and other cancer drug(s) such as a cRGD peptide, IL-12, a cRGD peptide and adriamycin. These agents, in different combinations, were bound either to the magnetic metal oxide surface, to the polymer inside the nanoparticle, or to both.

In addition to the therapeutic application, these sTRAIL-conjugated nanoparticles served as a marker for tumor imaging by MRI and/or fluorescence. By using these imaging modalities in animal models implanted with human glioma tumors, it was demonstrated that the sTRAIL-conjugated nanoparticles migrate to the site of the tumors and accumulate around and within the tumors, while the nanoparticles without bound sTRAIL migrate slower and accumulate only at the periphery of the tumor cells. The nanoparticles to which the sTRAIL was conjugated are used as a vehicle for stabilizing the sTRAIL, diagnosis of the tumor and assisting in targeting the tumors for inducing apoptosis. By using nanoparticles in which a fluorescent dye was bound to the polymer, it was further shown that the sTRAIL-conjugated nanoparticles identify and target infiltrating tumor cells. The ability of the sTRAIL-conjugated nanoparticles to specifically target glioma cells can be also employed for determining the border of the tumors in the brain and for distinguishing between recurrent gliomas and radiation-induced necrosis. In addition, the efficiency of the sTRAIL-conjugated nanoparticles for targeting and inducing apoptosis of tumor cells other then gliomas, e.g. carcinoma, breast cancer and lung cancer, was demonstrated.

The invention will now be illustrated by the following non-limiting Examples.

EXAMPLES

Example 1

Synthesis and Characterization of Gelatin/Iron Oxide Magnetic Composite Nanoparticles Gelatin/iron oxide magnetic composite nanoparticles of sizes ranging from ca. 5 nm up to 100 nm with narrow size distribution were prepared by nucleation followed by controlled growth of magnetic iron oxide thin films onto gelatin/iron oxide nuclei, as described in detail in WO 99/062079. The nucleation step was based on complexation of $Fe^{+2}$ ions to chelating sites of the gelatin, followed by partial oxidation (up to approximately 50%) of the chelated $Fe^{+2}$ to $Fe^{+3}$, so that the water soluble gelatin contained both chelated $Fe^{+2}$ and $Fe^{+3}$ ions. Gelatin/iron oxide nuclei were than formed by adding NaOH or, alternatively, ammonia aqueous solution up to ca. pH 9.5. The growth of magnetic films onto the gelatin nuclei accomplished by repeating several times the nucleation step.

Figure 2:
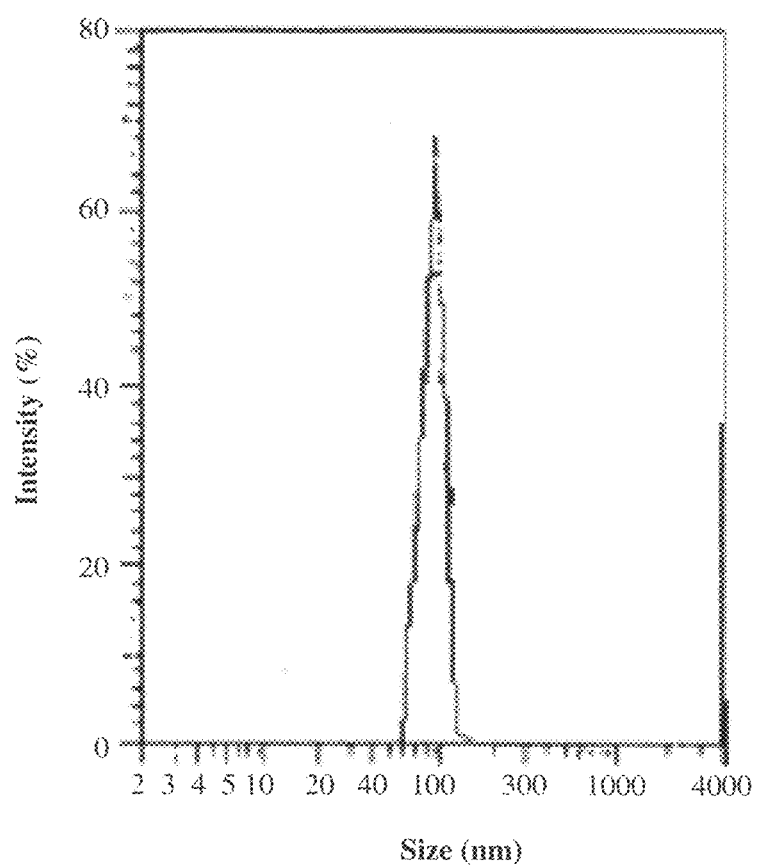
FIG. 2 shows a histogram of the diameter of gelatin/iron oxide composite nanoparticles prepared as described in Example 1 and dispersed in water.
Figure 3A:
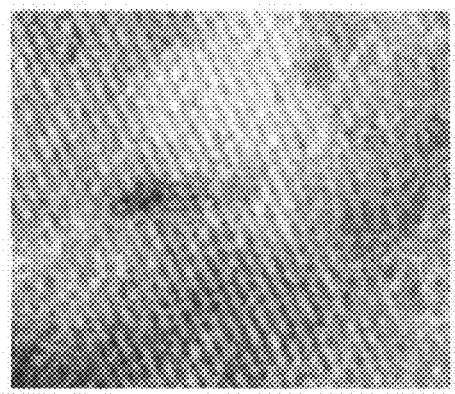
FIGS. 3A-3B show high resolution TEM (HTEM) (3A) and electron diffraction (ED) (3B) picture of gelatin/iron oxide magnetic composite nanoparticles prepared as described in Example 1.
Figure 3B:
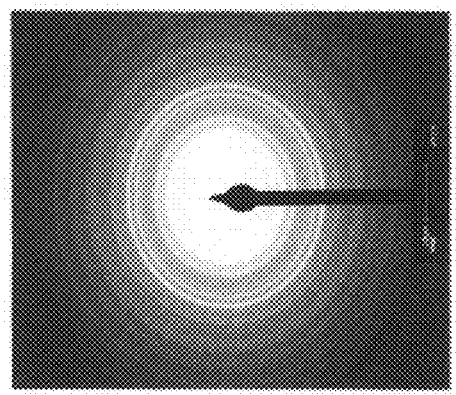
Figure 4:
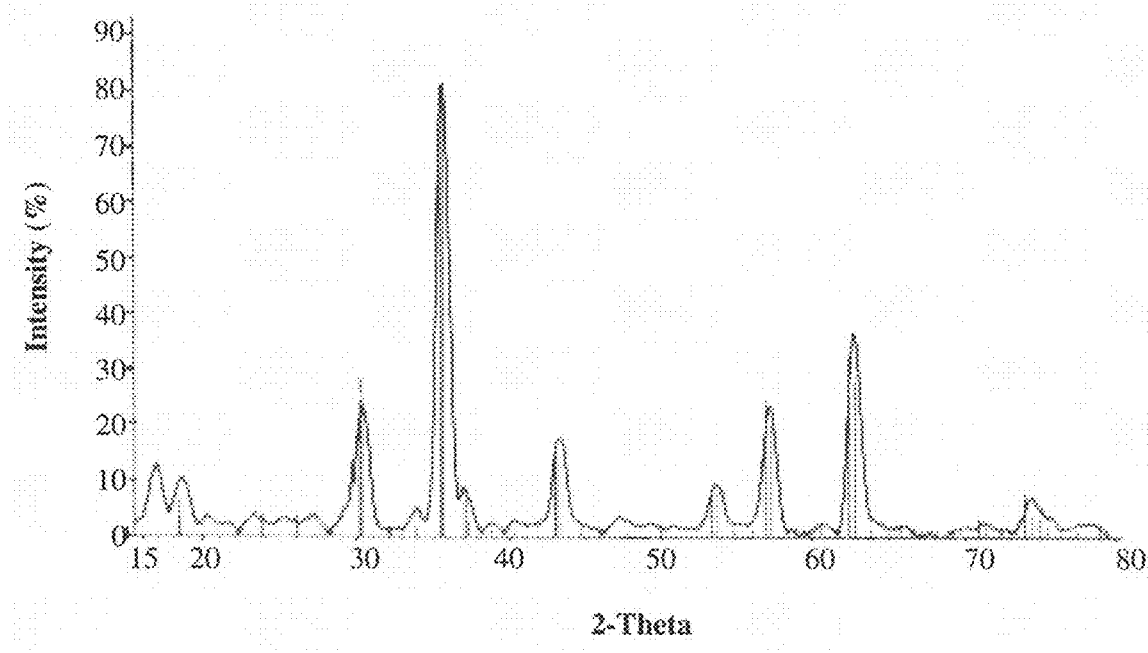
FIG. 4 shows X-ray diffraction (XRD) pattern of gelatin/iron oxide magnetic composite nanoparticles prepared as described in Example 1.
Figure 5:
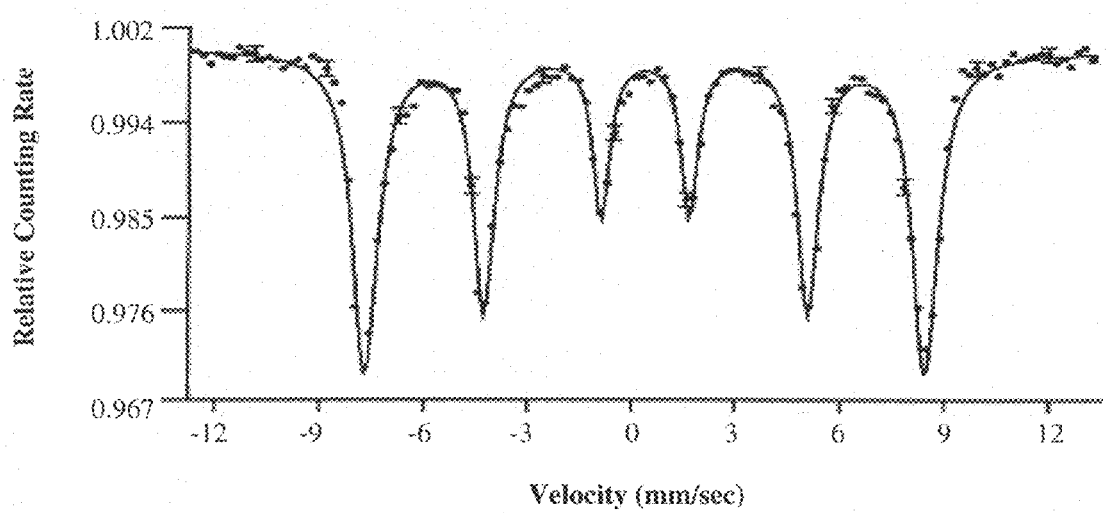
FIG. 5 shows mossbauer spectrum of gelatin/iron oxide magnetic composite nanoparticles prepared as described in Example 1.
Figure 6:
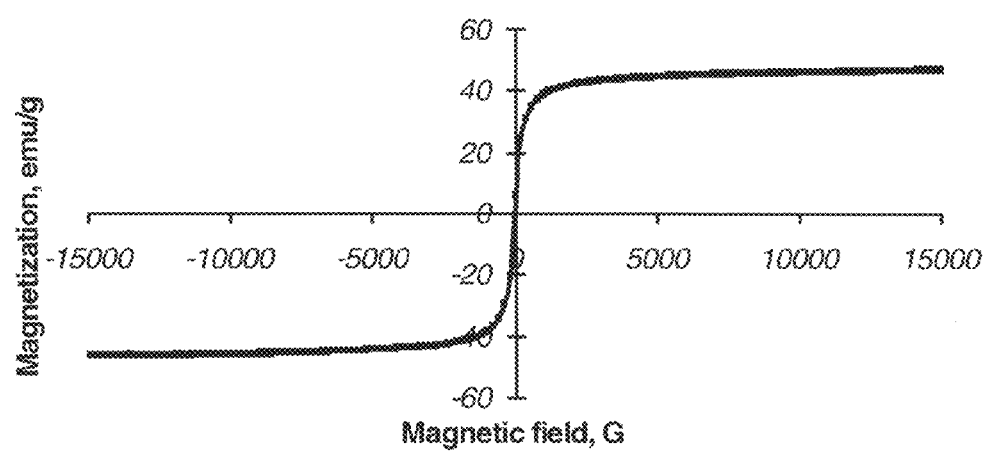
FIG. 6 shows room temperature magnetization (VSM) loop obtained for gelatin/iron oxide magnetic composite nanoparticles prepared as described in Example 1.

Briefly, nanoparticles of 15 nm average dry diameter were prepared by adding $FeCl_2$ solution (10 mmol/5 ml $H_2O$) to 80 ml aqueous solution containing 200 mg gelatin (Sigma), followed by $NaNO_2$ solution (7 mmol/5 ml $H_2O$). After a reaction time of 10 min, NaOH aqueous solution (1 N) was added up to pH 9.5. This procedure was repeated four times, or more, if larger particles were required. The formed magnetic nanoparticles were then washed from excess reagents using magnetic gradient columns. Surface analysis demonstrated the present of gelatin both within and on the surface of the nanoparticle. The surface gelatin provides additional stabilization against agglomeration to the nanoparticle and functional groups such as carboxilate and primary amines through which appropriate ligands can be covalently bonded. FIGS. 1A-1D demonstrate a transmission electron microscopy (TEM) picture of magnetic nanoparticles of increased average diameter formed by repeating the thin magnetic coating process during the growth step, 4 to 7 times, respectively. FIG. 2 shows that magnetic nanoparticles of 15 nm dry average diameter, prepared as described hereinabove and dispersed in water, posses one narrow population with hydrodynamic average diameter of ca. 100 nm. FIGS. 3A-3B show high resolution TEM (HTEM) picture (3A), demonstrating crystalline structure with d-spacing of 0.479 nm, and electron diffraction (ED) picture (3B), representing sharp rings indicating the crystalline character of the magnetic nanoparticles. FIG. 4 shows X-ray diffraction (XRD) pattern of the gelatin/iron oxide magnetic composite nanoparticles, indicating that the crystalline cores of these nanoparticles consist nearly completely of maghemite ($\gamma$-$Fe_2O_3$). From x-ray line broadening, one deduces a mean diameter of the magnetic cores of 15 nm. FIG. 5 shows mossbauer spectrum of the gelatin/iron oxide magnetic composite nanoparticles, further indicating that these nanoparticles consist of maghemite. It is assumed that magnetite ($Fe_3O_4$) nanoparticles were first produced by this nucleation and growth process, and were then oxidized to the more thermodynamic stable iron oxide, maghemite. FIG. 6 represents hysteresis loop at room temperature of the maghemite nanoparticles of 15 nm dry diameter, indicating that the M(H) curve of these nanoparticles does not exhibit any coercivity and does not saturate at 10,000 Oe, while the magnetic moment obtained at 10,000 Oe is ca. 41 emu $g^{-1}$. Both features are typical of superparamagnetic behavior.

Uniform gelatin/iron oxide magnetic composite nanoparticles of various sizes and properties were prepared by changing preparation conditions, e.g., oxidizing reagents, iron salt type, pH and temperature, as previously disclosed in WO 99/062079. Uniform nanoparticles of sizes smaller than 15 nm dry diameter down to 5 nm were prepared by gradual surface dissolution of the 15 nm nanoparticles with acids, e.g. HCl at pH ca. 1.0, or iron chelating ligands such as EDTA and oxalic acid. After achieving the desired diameter, the magnetic nanoparticles were wash into distilled water.

Example 2

Figure 7:
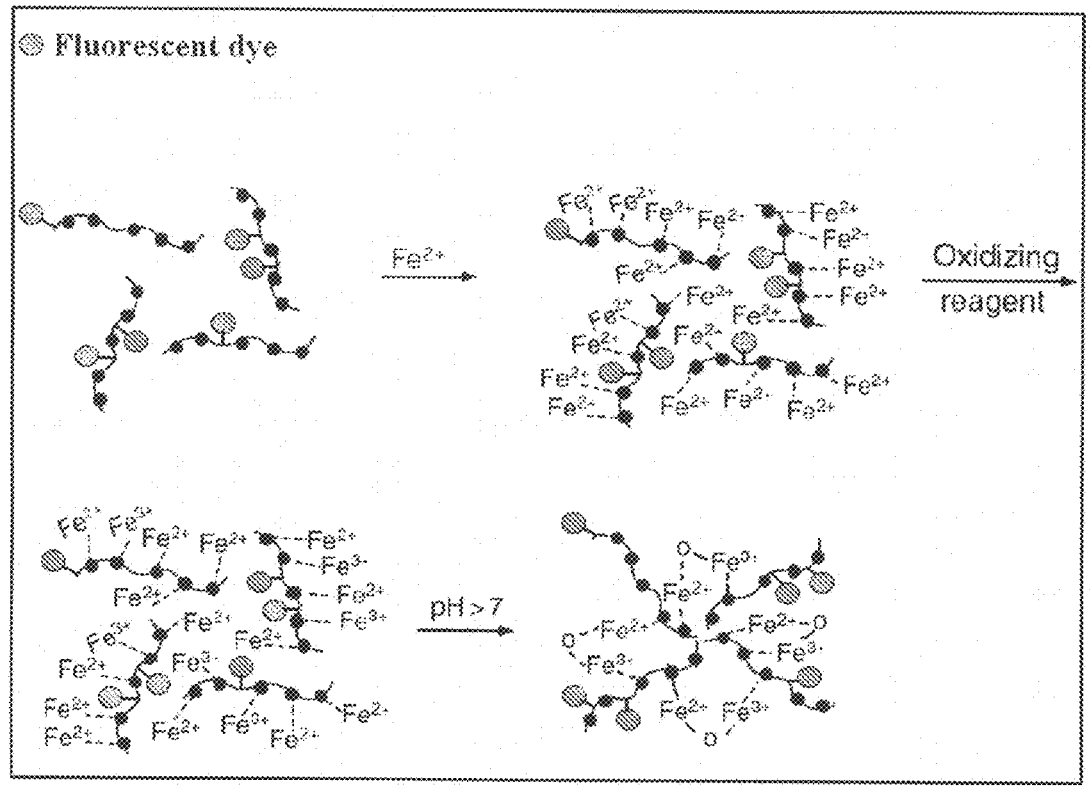
FIG. 7 illustrates the nucleation step of the preparation of fluorescent dye-labeled gelatin/iron oxide magnetic composite nanoparticles, as described in Example 2.

Synthesis of Fluorescent Dye-Labeled Gelatin/Iron Oxide Magnetic Composite Nanoparticles Fluorescent dye-labeled gelatin/iron oxide magnetic composite nanoparticles in which the fluorescent dye is mainly entrapped within the magnetic composite nanoparticles were prepared as described in Example 1, substituting the gelatin for gelatin covalently bound to a fluorescent dye, as illustrated in FIG. 7. For example, rhodamine-labeled nanoparticles were prepared by adding slowly 0.5 ml dimethyl sulfoxide (DMSO) containing 5 mg of rhodamine isothiocyanate (RITC) to 20 ml aqueous solution containing 200 mg gelatin. The pH of the aqueous solution was raised to 9.5 by adding NaOH aqueous solution (1 N), and the solution was shaken for 1 h at 60° C. This process involves the covalent binding, via thiourea and/or thiourethane bonds, between the part of the hydroxyl and amine groups of the gelatin and the isothiocyanate of the RITC. Excess of RITC was then removed from the gelatin conjugated rhodamine chains by extensive dialysis (cut off: 12-14000) of the former aqueous solution at 60° C. against $H_2O$, or by washing through a magnetic column. The volume of the solution was adjusted to 80 ml and the synthesis was then continued as described in Example 1.

A similar process was performed with other appropriate dyes, e.g. fluorescein.

Example 3

Synthesis of Drug(s) Containing Gelatin/Iron Oxide Magnetic Composite Nanoparticles Drug containing gelatin/iron oxide magnetic composite nanoparticles were prepared as described in Example 1, substituting the gelatin for gelatin covalently bound to the drug. For example, adriamycin (Aldrich) was covalently bound to the gelatin via the carbodiimide activation method, as described by Melamed and Margel (2001). Briefly, 123 mg NHS (N-hydroxysuccinimide, Sigma) and 82 mg CDC (1-cyclohexyl-3-(2-morpholinoethyl) carbodiimide metho-p-toluenesulfonate, Sigma) were added to 20 ml MES buffer (0.01 m at pH 5.0, Sigma) containing 200 mg gelatin and 5 mg adriamycin, and the solution was then shaken at 60° C. for 2 h. The solution was washed from excess reagent by dialysis (cut off: 12-14000) against water. The volume of the solution was adjusted to 80 ml and the synthesis was then continued as described in Example 1.

In a similar process, gelatin/iron oxide magnetic composite nanoparticles which methotrexate or/and sTRAIL, separately or in combination, was/were covalently bound to the gelatin, were prepared.

Example 4

Functionalization of Gelatin/Iron Oxide Magnetic Composite Nanoparticles

Various ways for generating functional groups on the surface of the gelatin/iron oxide magnetic composite nanoparticles prepared as described in Examples 1-3 have been developed, based on different principles such as (i) the high affinity of a coating polymer, e.g., dextran, to the nanoparticle surface; (ii) covalent binding between functional groups on the nanoparticles surface and a desired functional ligand, e.g., amino ligands such as proteins with activated double bonds on the nanoparticle surface via the Michael addition reaction or to carboxylate groups (belonging to the gelatin coating) via the carbodiimide activation method, as described by Melamed and Margel (2001); and (iii) precipitation of a coating polymer, e.g., gelatin or albumin, on the nanoparticle surface. The functional groups on the nanoparticle surface were then used for covalent or physical binding of the various drugs, e.g. TRAIL and cRGD peptide via different activation methods.

4(i) Functionalization with Activated Double Bonds

Divinyl sulfone (DVS) was added to the gelatin/iron oxide magnetic composite nanoparticles prepared as described in Examples 1-3, wherein the initial [DVS]/[nanoparticles] weight ratio was 4/1, and triethylamine was then added to reach a pH of 10.5, followed by incubation at 60° C. overnight. The formed functionalized gelatin/iron oxide-DVS or fluorescent dye-labeled gelatin/iron oxide-DVS nanoparticles were then washed with 0.1 M bicarbonate buffer (pH=8.3) by magnetic gradient columns, and stored at 4° C.

4(ii) Functionalization with Crosslinked Dextran Coating Containing Activated Double Bonds 2% (w/v) dextran (MW 48,000, Sigma) was added to an aqueous dispersion of gelatin/iron oxide magnetic composite nanoparticles prepared as described in Examples 1-3, and after dissolution of the dextran, the aqueous dispersion was shaken for 3 h at 85° C. The dextran coated nanoparticles were washed from excess dextran with water by magnetic columns. Crosslinking of the dextran coating was performed with DVS as described in 4(i) hereinabove, to prevent leakage of the physical adsorbed dextran into the aqueous continuous phase and for generation of surface activated double bonds.

4(iii) Functionalization with Gelatin or Albumin Coating in Absence or Presence of Activated Double Bonds 0.2% (w/v) gelatin was added to an aqueous dispersion of gelatin/iron oxide magnetic composite nanoparticles prepared as described in Examples 1-3, and the aqueous dispersion was then shaken for 3 h at 85° C. The aqueous dispersion was cooled to room temperature, and the gelatin-coated nanoparticles were then washed by magnetic columns. DVS derivatization was performed, if necessary, as described in 4(i) hereinabove.

An albumin coating on the nanoparticles was performed similarly, substituting the gelatin for bovine or human serum albumin.

Example 5

Immobilization of Drugs onto the Functional Gelatin/Iron Oxide Magnetic Composite Nanoparticles 5(i) Immobilization of Human TRAIL or IL12 onto Gelatin/Iron Oxide-DVS Magnetic Composite Nanoparticles 20 μg of human TRAIL (hTRAIL, CytoLab Ltd., Israel) was added to 1 ml bicarbonate buffer dispersion (0.1 M, pH=8.3) containing 1 mg gelatin/iron oxide magnetic composite nanoparticles, prepared as described in Example 4, and the dispersion was then mixed at room temperature for 60 min. This process involves the binding, via Michael addition, of residual double bonds of the nanoparticles and primary amino groups of the TRAIL. Blocking of residual activated double bonds was then performed with glycine, by adding glycine (1% w/v) and continuing mixing the dispersion for additional 60 min at room temperature. Excess of unbound hTRAIL and glycine were removed with PBS (pH=7.4) by magnetic gradient columns. The concentration of bound hTRAIL, determined by ELISA Development Kit (900-K141 lot no. 11041410, CytoLab Ltd., Israel), was found to be ca. 2000 ng/mg nanoparticles.

IL12 was bound onto the gelatin/iron oxide-DVS magnetic composite nanoparticles similarly, substituting the hTRAIL for IL12.

5(ii) Immobilization of cRGD Peptide onto Gelatin/Iron Oxide-DVS Magnetic Composite Nanoparticles The experiment described in 5(i) hereinabove was repeated substituting the μg of hTRAIL for 3 mg of the cRGD peptide of the sequence cyclo (Arg-Gly-Asp-D-Phe-Lys (SEQ ID NO: 1) (Peptides International, Louisville, Ky. 40224 USA). For negative control, a similar process was performed substituting the cRGD peptide for the cRAD peptide of the sequence cyclo (Arg-Ala-Asp-D-Phe-Lys, Peptides International).

5(iii) Immobilization of hTRAIL and a cRGD Peptide onto Gelatin/Iron Oxide-DVS Magnetic Composite Nanoparticles The experiment described in 5(i) hereinabove was repeated substituting the glycine for 3 mg cRGD peptide, and as a consequence, the remaining residual activated double bonds of the DVS were conjugated to the cRGD peptide.

5(iv) Immobilization of Bioactive Reagents, e.g., hTRAIL and/or cRGD Peptide, onto Gelatin/Iron Oxide Composite Nanoparticles Human TRAIL and/or cRGD peptide were covalently bound to the gelatin/iron oxide composite nanoparticles prepared according to Examples 1-3 and Example 4(iii) via the carbodiimide activation method, as described in Melamed and Margel (2001). Briefly, 123 mg NHS and 82 mg CDC were added to 20 ml MES buffer (0.01 M at pH 5.0, Sigma) containing 200 mg nanoparticles, and the nanoparticles dispersion was then shaken at room temperature for 3 h. The activated nanoparticles were washed extensively by magnetic gradiant columns with PBS, and 5 ml PBS solution containing 8 mg hTRAIL or 50 mg cRGD peptide were then added to 20 ml of the washed activated nanoparticles dispersion. The suspension was shaken at room temperature for about 8 h, and blocking of residual activated groups was then performed with either glycine (200 mg) or cRGD peptide (50 mg) as described in 5(i) or 5(iii), respectively.

5(v) Immobilization of Avastin or Remicade onto Gelatin/Iron Oxide-DVS Magnetic Composite Nanoparticles 20 μg of the monoclonal antibodies Avastin (Bevacizumab, Genentech) or Remicade (Infliximab) is added to 1 ml bicarbonate buffer dispersion (0.1 M, pH=8.3) containing 1 mg gelatin/iron oxide magnetic composite nanoparticles, prepared as described in Example 4, and the dispersion is then mixed at room temperature for 60 min. This process involves the binding, via Michael addition, of residual double bonds of the nanoparticles and primary amino groups of the Avastin or Remicade. Blocking of residual activated double bonds is then performed with glycine, by adding glycine (1% w/v) and continuing mixing the dispersion for additional 60 min at room temperature. Excess of unbound Avastin or Remicade and glycine are removed with PBS (pH=7.4) by magnetic gradient columns.

5(vi) Physical Immobilization of Bioactive Reagents, e.g., hTRAIL, onto Gelatin/Iron Oxide Magnetic Composite Nanoparticles 20 μg of human TRAIL (hTRAIL, CytoLab Ltd., Israel) was added to 1 ml bicarbonate or PBS buffer dispersion (0.1 M, pH=8.3) containing 1 mg non-functionalized gelatin/iron oxide magnetic composite nanoparticles prepared as described in Example 3, or albumin coated gelatin/iron oxide magnetic composite nanoparticles prepared as described in example 4(iii). The dispersion was then mixed at room temperature for 120 min, and as a consequence, the hTRAIL was non-covalently bound the non-coated, or albumin coated, nanoparticles. This physical binding is based on non-covalent interactions, e.g., hydrophobic bonds, ionic interactions and hydrogen bonds, between the TRAIL and the nanoparticles. Excess of unbound hTRAIL were removed with PBS (pH=7.4) by magnetic gradient columns.

5(vii) Immobilization of Human TRAIL onto Gelatin/Iron Oxide Magnetic Composite Nanoparticle Human sTRAIL was bound directly to the gelatin/iron oxide nanoparticles via the carbodiimide activation method, as described by Melamed and Margel (2001). In a typical experiment, 123 mg NHS and 82 mg CDC were added to 15 ml MES buffer (0.1M at pH 5.0) containing 10 mg nanoparticles. The nanoparticles mixture was then shaken at room temperature for ca. 3 h. The activated nanoparticles were washed by magnetic gradient columns. PBS solution (2 ml) containing 0.5 mg sTRAIL was then added to 8 ml of the washed activated nanoparticles PBS dispersion. The dispersion was then shaken at room temperature for ca. 2 h. Blocking of residual activated double bonds was then performed with glycine or primary amino polyethylene glycol, by adding glycine (1% w/v) (or primary amino polyethylene glycol, 5 mg) and continuing mixing the dispersion for additional 60 min at room temperature. Excess of unbound hTRAIL and glycine (or amino polyethylene glycol) were removed with PBS (pH=7.4) by magnetic gradient columns.

The concentrations of the bound bioactive agents described in 5(i) to 5(vi) were controlled by changing binding parameters, e.g. hTRAIL concentration.

Example 6

In Vitro Studies: Targeting, Imaging and Apoptosis of Glioma Cells

Materials and Methods

Cell lines. All the cells used in the following experiments were obtained from the American Tissue Culture Collection (ATCC) or from the Hermelin Brain Tumor Center (Henry Ford Hospital, Detroit, Mich.). All cells were cultured in DMEM supplemented with 10% FBS (Hyclone, Logan, Utah), 2 mM L-glutamine and 100 ug/ml streptomycin-penicillin (Invitrogen) at 37° C. under 5% $CO_2$.

Measurements of cell apoptosis. Cell apoptosis was measured using propidium iodide (PI) staining and analyzed by flow cytometry as described by Riccardi and Nicoletti (2006) as well as by ELISA (Cell Death Detection ELISA Kit) using anti-histone antibodies as described by Blass et al. (2002). Cells ($10^6$/ml) were plated in six-well plates at 37° C. and treated by the indicated treatments (addition of 10 μl or less phosphate-buffered saline (PBS) or PBS containing the peptide, e.g. TRAIL, or unbound or peptide bound nanoparticles) for 24 h. Detached cells and trypsinized adherent cells were pooled, fixed in 70% ethanol for 1 h on ice, washed with PBS and treated for 15 min with RNase (50 μM) at room temperature. Cells were then stained with PI (5 μg/ml) and analyzed on a Becton-Dickinson cell sorter.

Cell viability was further quantitatively assessed by the measurement of the cytoplasmatic enzyme lactate dehydrogenase (LDH) released from dead cells to the medium (kit purchased from Sigma). For this purpose, supernatants were collected from control and treated cells, and following centrifugation (10 min 1,400×g), supernatants were transferred to 96-well plates and LDH was measured according to the manufacturer's instructions.

Figure 8:
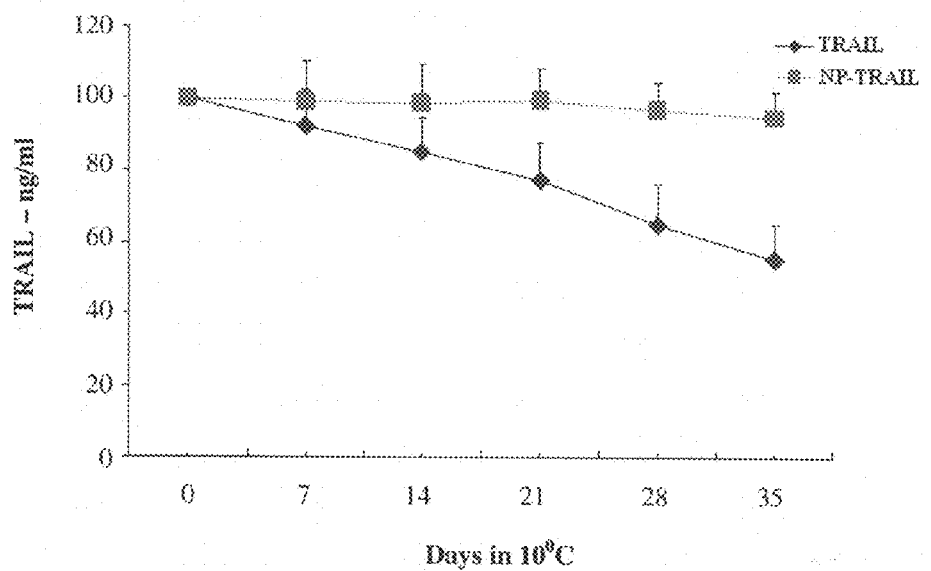
FIG. 8 shows the stability of free tumor necrosis factor-related apoptosis-inducing ligand (TRAIL) vs. TRAIL conjugated to gelatin/iron oxide magnetic composite nanoparticles (NP-TRAIL), at 10° C. during 35 days.

6(i) Stabilization of TRAIL by Conjugation to Gelatin/Iron Oxide Magnetic Composite Nanoparticles In order to examine the stability of the free and conjugated TRAIL against degradation, 1 ml PBS containing either free TRAIL (100 ng) or TRAIL-conjugated gelatin/iron oxide magnetic composite nanoparticles (NP-TRAIL, 100 ng TRAIL) were incubated at 10° C., and the concentration of TRAIL was measured during 35 days. FIG. 8 shows that the conjugation of TRAIL to the nanoparticles stabilized the TRAIL so that the original concentration of the conjugated TRAIL was maintained up to 35 days in 10° C. In contrast, the free TRAIL significantly degraded under these conditions.

Figure 9A:
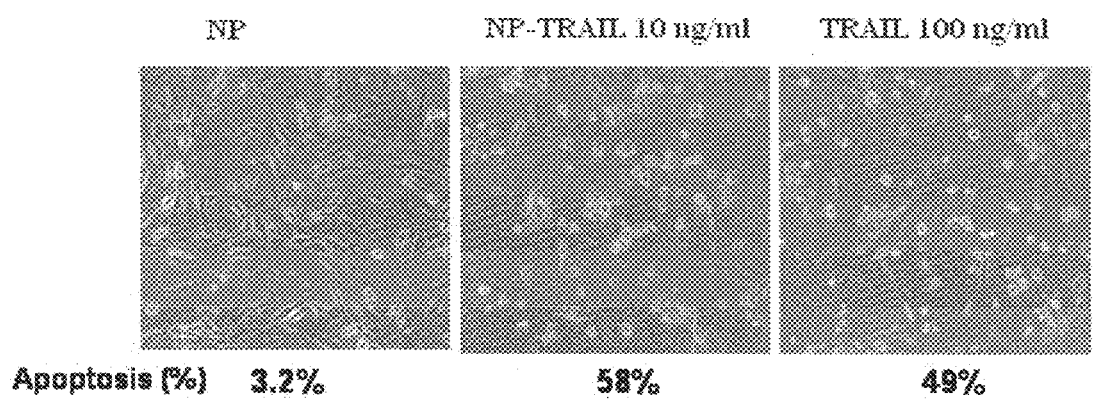
FIGS. 9A-9B show the apoptosis in human A172 glioma cells (9A) and in glioma spheres established from primary HF2020 tumors (9B) induced by gelatin/iron oxide magnetic composite nanoparticles (NP), free TRAIL (100 ng/ml) and TRAIL-conjugated gelatin/iron oxide magnetic composite nanoparticles (NP-TRAIL, 10 ng/ml).

6(ii) TRAIL-Conjugated Gelatin/Iron Oxide Magnetic Composite Nanoparticles Induce Apoptosis in Human Glioma Cells and in Glioma Spheres Established from Primary Tumors Human glioma cells A172 were incubated with either TRAIL (100 ng/ml) or NP-TRAIL (10 ng TRAIL/ml) for 5 hours. Cell apoptosis was determined by propidium iodide staining and analyzed by both flow cytometry (FACS) and the morphological appearance of the cells. FIG. 9A shows that free TRAIL induced apoptosis of about 48% of the cells whereas the NP-TRAIL induced apoptosis of about 57% of the cells and the nanoparticles alone did not induce significant cell apoptosis. In other words, the apoptosis activity induced by the conjugated TRAIL was at least 10 times higher than that induced by the free one.

Figure 9B:
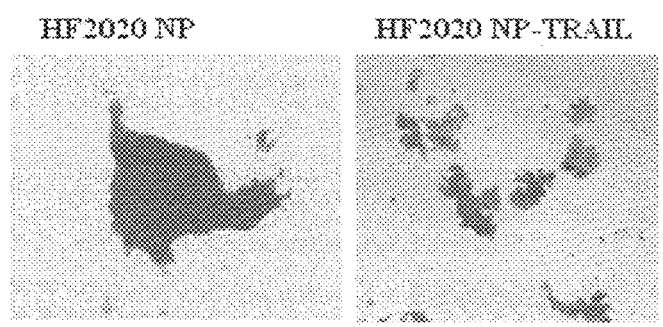
Figure 10:
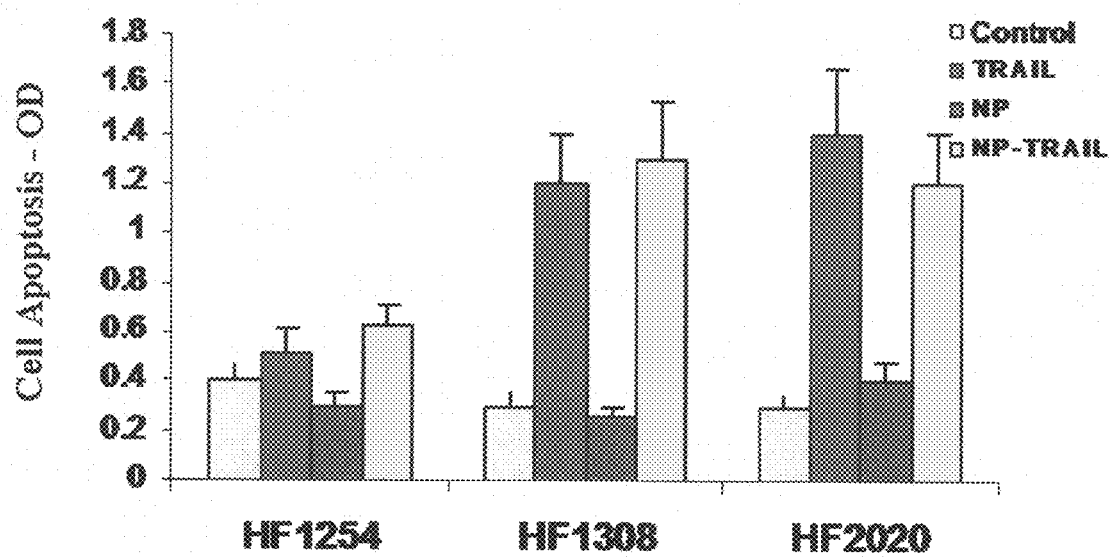
FIG. 10 shows the effect of free TRAIL and TRAIL-conjugated gelatin/iron oxide magnetic composite nanoparticles (NP-TRAIL) on the apoptosis of glioma spheroids established from the human glioma specimens HF1254, HF1308 and HF2020. Spheroids were plated in 24-well plates and were treated with medium (Control), TRAIL (100 ng/ml), gelatin/iron oxide magnetic composite nanoparticles (NP) and TRAIL-conjugated gelatin/iron oxide magnetic composite nanoparticles (NP-TRAIL, 10 ng/ml). Cell death was determined after 24 h of treatment using LDH assay. The results are the mean±SE of triplicates in two different experiments.

The apoptotic effect of free TRAIL (100 ng/ml) and NP-TRAIL (10 ng TRAIL/ml) was further tested using glioma spheroids derived from three different tumors, i.e., HF2020, HF1254 and HF1308. These cultures resemble more the original tumors as they maintain their three dimensional structure and cell-cell interaction. As found, glioma spheroids derived from HF2020, shown in FIG. 9B, and HF1308 underwent cells apoptosis in response to TRAIL or NP-TRAIL, whereas HF1254 underwent only a low degree of cell apoptosis. In particular, as presented in FIG. 9B and FIG. 10, both TRAIL and NP-TRAIL significantly increased the level of LDH in the HF2020 and the HF1308 glioma spheroids.

Figure 11:
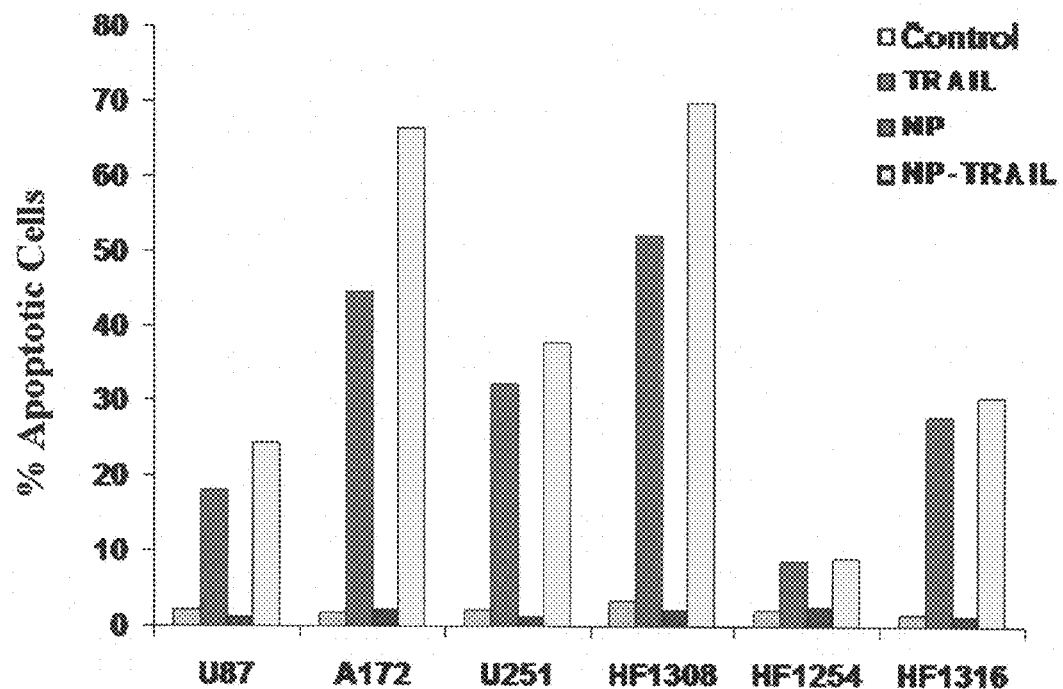
FIG. 11 shows the cytotoxic effect of free TRAIL (100 ng/ml) and TRAIL-conjugated gelatin/iron oxide magnetic composite nanoparticles (NP-TRAIL, 10 ng TRAIL/ml) on glioma cells U87, A172 and U251, as well as on primary cultures of glioma cells HF1308, HF1254 and HF1316. Gelatin/iron oxide magnetic composite nanoparticles (NP) alone or PBS (Control) served as controls. Cell death was determined after 24 h of treatment by FACS analysis.

6(iii) The Cytotoxic Effect of Free TRAIL and TRAIL-Conjugated Gelatin/Iron Oxide Magnetic Composite Nanoparticles in Various Glioma Cell Lines and Glioma Primary Cultures Glioma cells U87, A172 and U251, as well as primary cultures of glioma cells HF1308, HF1254 and HF1316, were incubated with TRAIL (100 ng/ml), NP-TRAIL (10 ng TRAIL/ml) or gelatin/iron oxide magnetic composite nanoparticles (NP) alone for 24 h. The cells were then collected, stained with propidium iodide and analyzed for the sub-$G_0$ population (apoptotic cells) by FACS analysis. FIG. 11 shows that for all cases, the cytotoxic effect of NP alone did not differ from the effect caused by PBS, and that NP-TRAIL exhibited significantly higher cytotoxic activity than that of free TRAIL.

Figure 12:
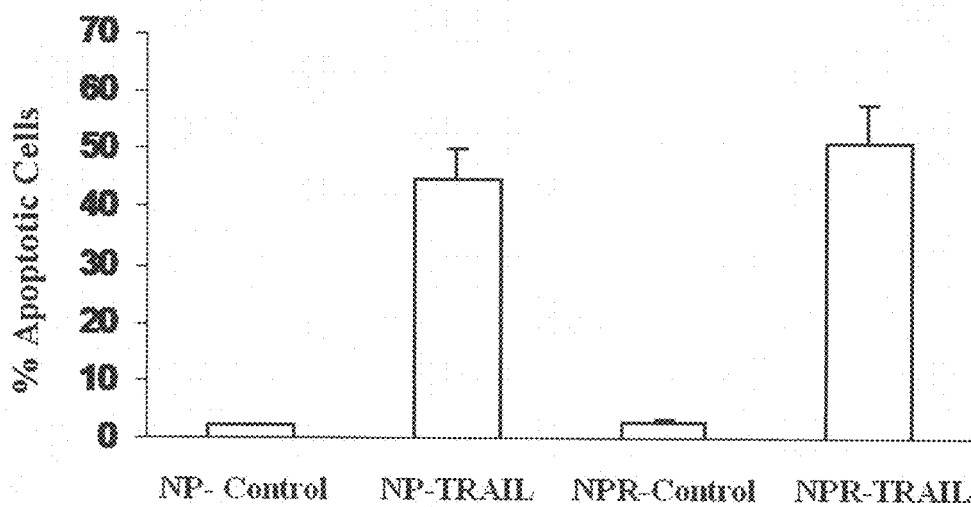
FIG. 12 shows the cytotoxic effect of TRAIL-conjugated to non-fluorescent or fluorescent dye-labeled gelatin/iron oxide magnetic composite nanoparticles on A172 cells. A172 cells were incubated for 5 h with control nanoparticles (NP-Control), TRAIL-conjugated non-fluorescent nanoparticles (NP-TRAIL), control rhodamine-labeled nanoparticles (NPR-Control) or TRAIL-conjugated rhodamine-labeled nanoparticles (NPR-TRAIL). Cell apoptosis was determined using propidium iodide staining and FACS analysis, and the results are the mean±SE of three different experiments.

6(iv) The Cytotoxic Effect of TRAIL-Conjugated Non Fluorescent and Fluorescent Dye-Labeled Gelatin/Iron Oxide Magnetic Composite Nanoparticles in Various Glioma Cells Human glioma cells A172 cells were incubated for 5 h with non-fluorescent nanoparticles (NP-Control), NP-TRAIL (10 ng TRAIL/ml), rhodamine-labeled gelatin/iron oxide magnetic composite nanoparticles (NPR) and TRAIL-conjugated rhodamine-labeled gelatin/iron oxide magnetic composite nanoparticles (NPR-TRAIL, 10 ng TRAIL/ml). Apoptosis was determined using propidium iodide staining and FACS analysis. As shown in FIG. 12, the apoptosis induced by NPR-TRAIL (51%) was similar to that induced by NP-TRAIL (45%). Similar results were observed also for other glioma cells, e.g., U251 and U87. These results illustrate that the fluorescent TRAIL-conjugated nanoparticles induce apoptosis of glioma cells similar to their non-fluorescent counterparts and about 10 times more than that of free TRAIL.

Figure 13:
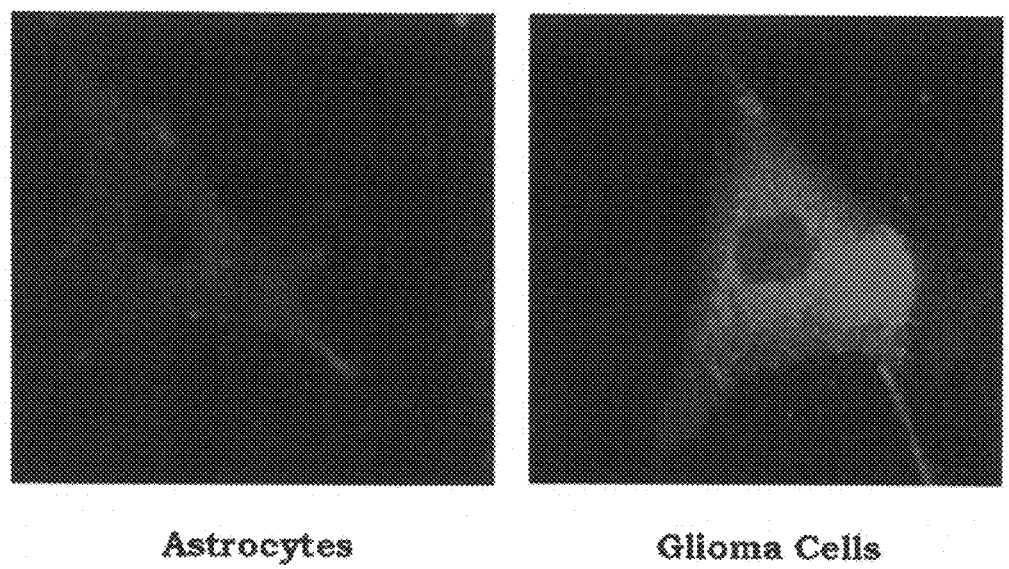
FIG. 13 shows the specific internalization of TRAIL-conjugated rhodamine-labeled gelatin/iron oxide magnetic composite nanoparticles (NPR-TRAIL) into glioma cells as compared to normal astrocytes. NPR-TRAIL were incubated with A172 cells and with normal astrocytes for 30 min, and the immunofluorescence of the cells was determined using a confocal microscopy. The results represent one out of three experiments which gave similar results.

6(v) Specific Internalization of the Fluorescent TRAIL-Conjugated Gelatin/Iron Oxide Magnetic Composite Nanoparticles into Glioma Cells The specificity of NP-TRAIL for glioma cells as compared to normal astrocytes was examined with NPR-TRAIL. In particular, human glioma cells A172 and normal human astrocytes were incubated with NPR-TRAIL (10 ng TRAIL/ml) for 30 min and the cells were viewed and photographed using confocal microscopy. As shown in FIG. 13, NPR-TRAIL entered the A172 cells within 30 min of treatment and accumulated in the ER/golgi region, whereas very weak fluorescent was observed in the normal astrocytes. Similarly, NPR that were not conjugated to TRAIL did not enter the cells in both cell types (data not shown). These results indicate that NPR-TRAIL probably entered the glioma cells via internalization following binding to TRAIL receptors, and they may have important implications for the ability of TRAIL-conjugated nanoparticles to deliver drugs into the cells.

Figure 14:
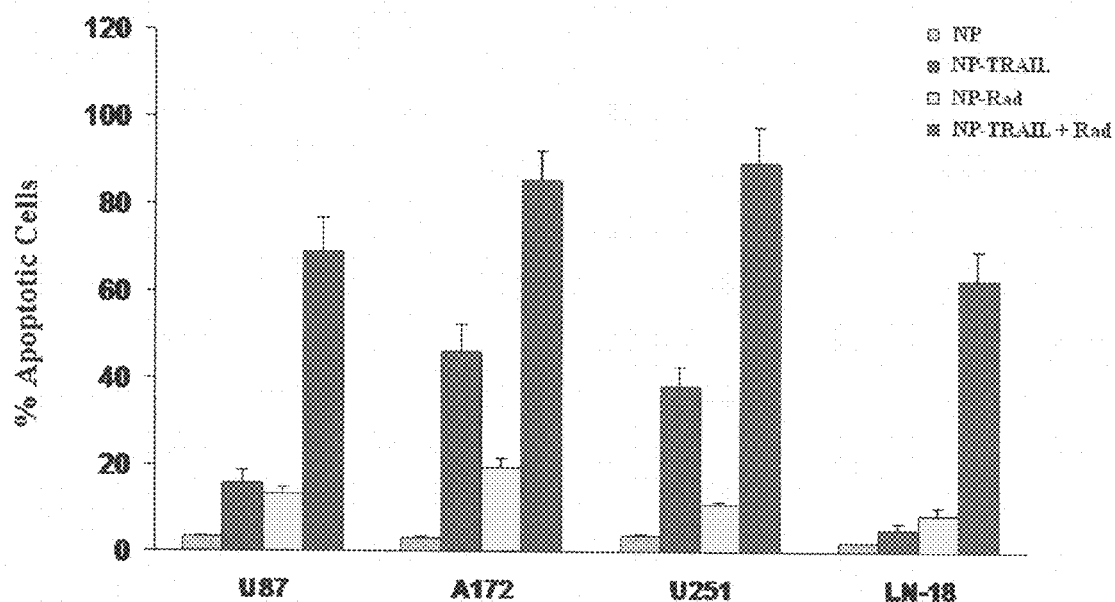
FIG. 14 shows synergistic effect of γ-irradiation and TRAIL-conjugated gelatin/iron oxide magnetic composite nanoparticles (NP-TRAIL) on U87, A172, U251 and LN-18 glioma cell lines. Cells were incubated with NP-TRAIL (5 ng TRAIL/ml) or with gelatin/iron oxide magnetic composite nanoparticle (NP) alone for 24 hr, or γ-irradiated (10 Gy for 2 h) and then treated with NP-TRAIL (NP-TRAIL+Rad, 5 ng TRAIL/ml) or with NP alone (NP-Rad) for 24 h. Cell apoptosis was determined by FACS analysis.

6(vi) Synergistic Effect of γ-Irradiation and TRAIL-Conjugated Gelatin/Iron Oxide Magnetic Composite Nanoparticles Although NP-TRAIL induced apoptosis in many glioma cell lines, there were some glioma cells that were resistant to this treatment. Thus, and as γ-radiation has been reported to increase the sensitivity of tumor cells to TRAIL by increasing the expression of TRAIL receptors, the effect of combined treatment with NP-TRAIL and γ-radiation on glioma cell apoptosis was examined. In particular, A172 and U251 cells that were sensitive to TRAIL, as well as U87 cells that exhibited low response to TRAIL and LN-18 cells that were resistant to TRAIL treatment, were employed, and sub-optimal concentration of NP-TRAIL (5 ng TRAIL/ml) and γ-radiation (10 Gy) were used. Cells were treated with NP alone, NP-TRAIL (5 ng TRAIL/ml), γ-radiation (10 Gy), or a combination of NP-TRAIL (5 ng TRAIL/ml) and γ-radiation (10 Gy). For the combined treatment, cells were first irradiated and after 2 h were treated with NP alone or with NP-TRAIL. Cell apoptosis was determined 24 h later. FIG. 14 shows that the apoptosis induced by the combined treatment was significantly increased and that the addition of low dosage of γ-irradiation overcame the resistance of some glioma cells to NP-TRAIL.

Figure 15:
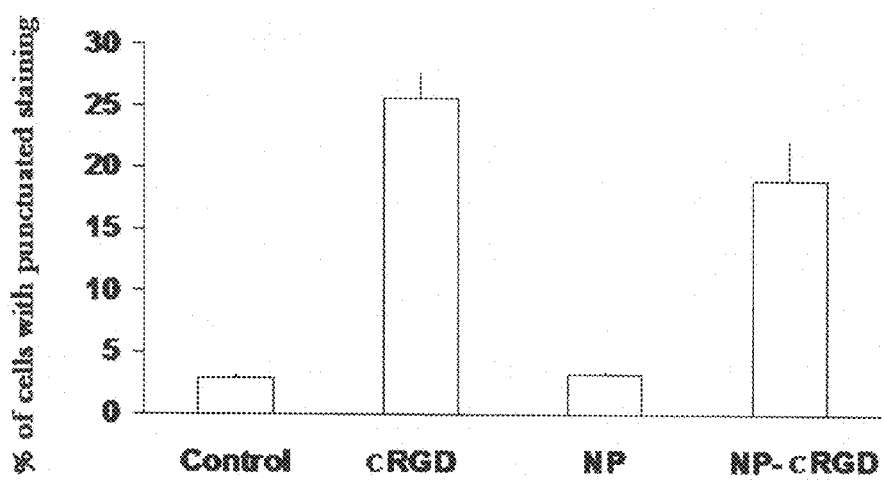
FIG. 15 shows that both cRGD peptide (cRGD) and cRGD peptide-conjugated gelatin/iron oxide magnetic composite nanoparticles (NP-cRGD) induce autophagy, i.e., an increase of punctuated staining, in glioma U251 cells, compared with control or gelatin/iron oxide magnetic composite nanoparticles (NP) only-treated cells.

6(vii) cRGD Peptide-Conjugated Gelatin/Iron Oxide Magnetic Composite Nanoparticles Induce Autophagy in Glioma Cells Another type of cell death induced in glioma cells is type II cell death or autophagy, as described in Gozuacik and Kimchi (2004). In order to characterize autophagy, cells were transfected with LC3-GFP plasmid and the accumulation of autophagic vacuolization was examined. As found, whereas in the control cells IC3-GFP appeared throughout the cells, in autophagic cells punctuate staining was observed. In view of that, the pattern of LC3-GFP in the control cells treated with NP only and in the cells treated with cRGD peptide-conjugated gelatin/iron oxide magnetic composite nanoparticles (NP-cRGD) was examined. For this purpose, U251 cells were transfected with LC3-GFP for 24 h, the cells were treated with cRGD peptide (10 μg/ml), NP only or NP-cRGD (ca. 4 μg cRGD/ml) for additional 24 h, and the percentage of cells with punctuated GFP staining was then calculated. As shown in FIG. 15, about 24 h, about 30% of the cRGD-treated cells and about 18% of the NP-cRGD-treated cells exhibited an increased punctuated pattern of LC3-GFP. Contrary to that, only 2-3% of the control or NP-treated cells exhibited punctuated staining.

6(viii) Synergistic Effect of TRAIL and cRGD Peptide-Conjugated Gelatin/Iron Oxide Magnetic Composite Nanoparticles In this experiment, LN-18 cells that were resistant to TRAIL treatment were incubated for 24 h with NP-TRAIL, TRAIL and cRGD peptide-conjugated nanoparticles (prepared as described in Example 5(iii)) or adriamycin containing TRAIL and cRGD peptide-conjugated nanoparticles (prepared as described in Examples 3 and 5(iii)). The synergistic effect of the additional drugs (cRGD peptide and adriamycin) was demonstrated by significant increased in the apoptosis percent, which was about 8% for the NP-TRAIL, about 25% for the TRAIL and cRGD peptide-conjugated nanoparticles, and 45% for the adriamycin containing TRAIL and cRGD peptide-conjugated nanoparticles.

Figure 16:
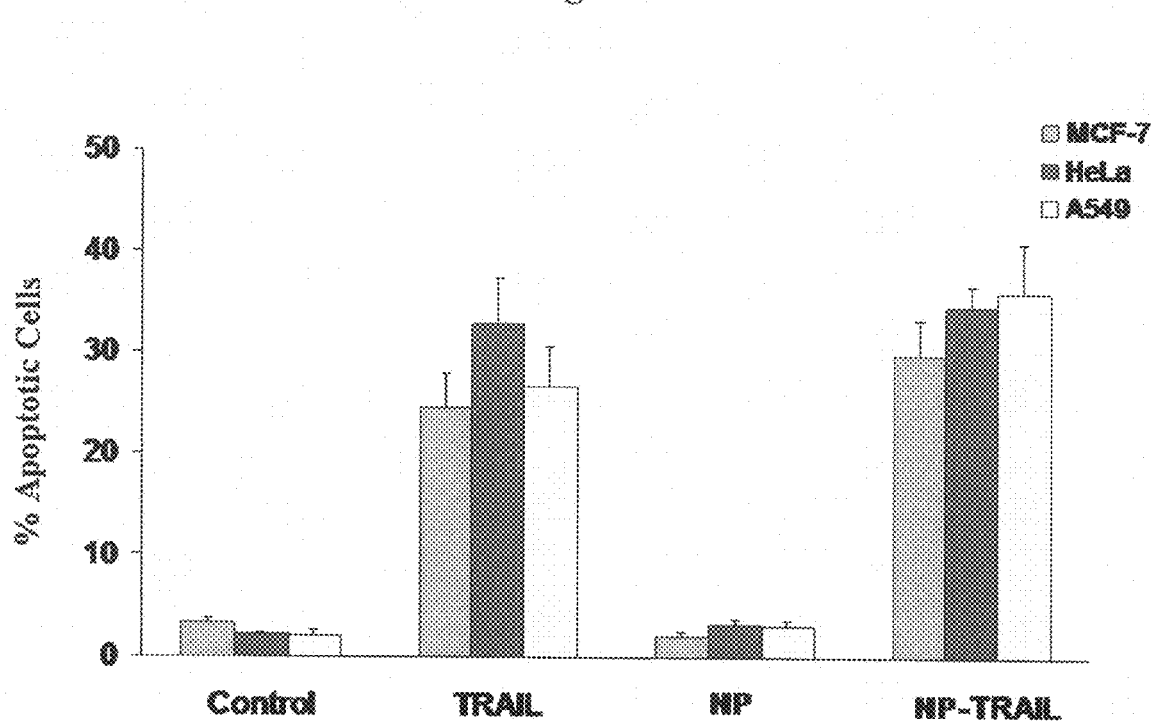
FIG. 16 shows the effect of TRAIL-conjugated gelatin/iron oxide magnetic composite nanoparticles (NP-TRAIL) on apoptosis of cervical carcinoma cell line HeLa, breast cancer cell line MCF-7 and lung cancer cells A549. The various cell lines were incubated with TRAIL (100 ng/ml), NP-TRAIL (50 ng TRAIL/ml), nanoparticles (NP) alone or PBS (Control) for 24 h, and data is shown as mean±SE.

6(ix) Effect of TRAIL-Conjugated Conjugated Gelatin/Iron Oxide Magnetic Composite Nanoparticles on Apoptosis of Various Tumor Cells In this experiment, the effect NP-TRAIL on tumor cells other than glioma was examined, using the cervical carcinoma cell line HeLa, the breast cancer cell line MCF-7 and the lung cancer cells A549. FIG. 16 shows the apoptotic effect of TRAIL (100 ng/ml), NP-TRAIL (50 ng TRAIL/ml), NP alone or PBS (control) after incubation time of 5 h. As shown, whereas both PBS and NP had insignificant apoptotic effect, NP-TRAIL induced a significant apoptosis that was at least twice of that induced by TRAIL, indicating that conjugation of TRAIL to the nanoparticles maintained its apoptotic effect and even increased it towards various cancer cells. Cell apoptosis was measured using propidium iodide (PI) staining and analyzed by flow cytometry.

6(x) Synergistic Effect of γ-Irradiation and TRAIL-Conjugated Gelatin/Iron Oxide Magnetic Composite Nanoparticles on Human Glioma Stem Cell Spheres Glioma stem cells were established from the tumor specimens 2355 and 2303, were grown as spheroids and maintained in culture for two months. The glioma stem cells exhibited self-renewal and differentiated on poly-L-Lysine to astrocytes, neurons and oligodendrocytes. In order to examine the effect of NP and of NP-TRAIL on the cells, spheroids were placed in a 6-well plate and were treated with TRAIL (100 ng/ml), NP alone or NP-TRAIL (50 ng TRAIL/ml) for 24 h. The supernatants were then collected and LDH analysis was performed.

Figure 17A:
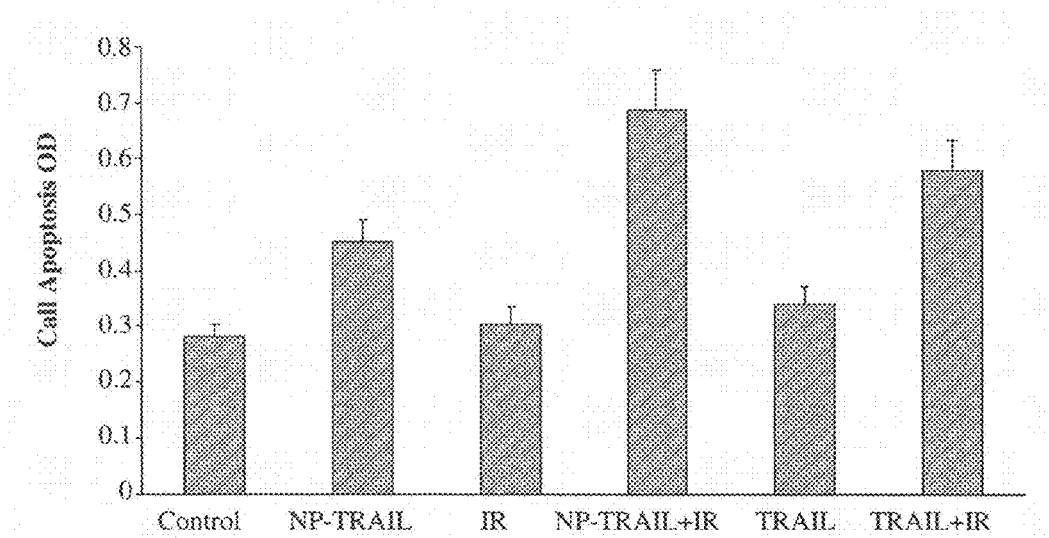
FIGS. 17A-17B show synergistic effect of γ-irradiation and TRAIL-conjugated gelatin/iron oxide magnetic composite nanoparticles (NP-TRAIL) on glioma stem cells spheroids established from the tumor specimens 2355 (17A) and 2303 (17B). Cells were treated with either TRAIL (100 ng/ml), the nanoparticles (NP) alone (Control) or NP-TRAIL (50 ng/ml) for 24 h, the supernatants were then collected and LDH analysis was performed. In order to evaluate the combined effect of irradiation (IR) and TRAIL, cells were first irradiated with 5 Gy radiation and after 4 h were treated either with TRAIL or NP-TRAIL for additional 24 h. Cell death was determined using LDH levels in culture supernatants. The results represent one experiment that was done in triplicate out of three similar experiments.
Figure 17B:
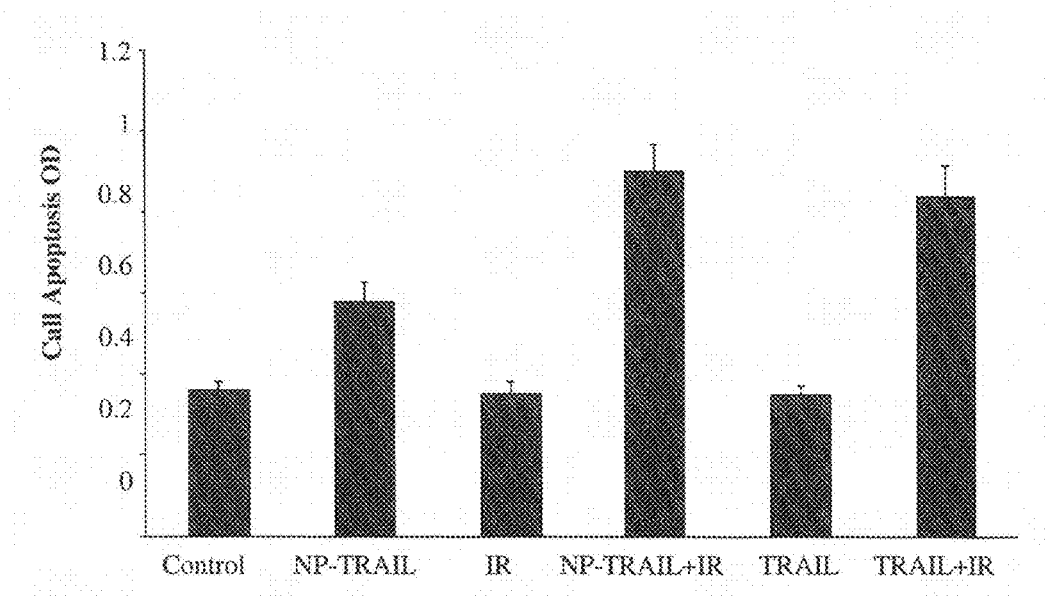

In order to evaluate the combined effect of γ-radiation and TRAIL, the cells were first irradiated with 5 Gy radiation and after 4 hours were treated with either TRAIL or NP-TRAIL for additional 24 h. Cell death was determined using LDH levels in culture supernatants. The apoptotic effect induced by the different treatments was similar in both glioma stem cell lines and illustrated in FIGS. 17A-17B. Insignificant apoptotic effect was observed for NP only, γ-irradiation alone or free TRAIL. NP-TRAIL induced moderate apoptotic effect; however, both NP-TRAIL and free TRAIL, together with γ-irradiation, induced significant apoptosis.

Figure 18:
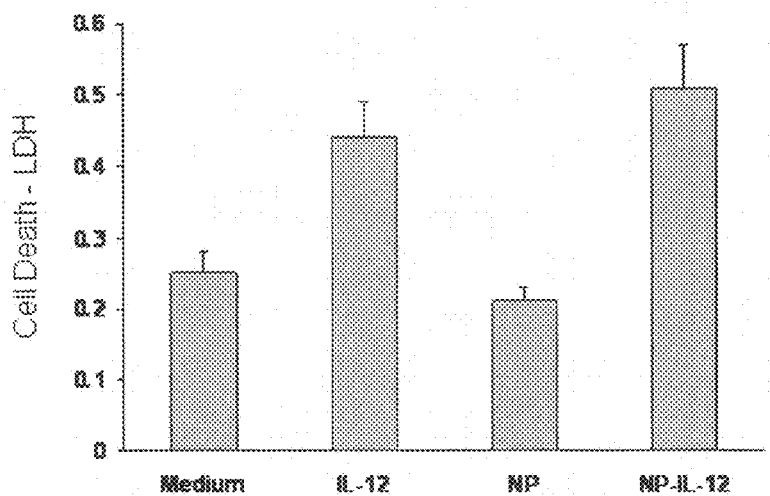
FIG. 18 shows the effect of IL-12 and IL-12-conjugated gelatin/iron oxide magnetic composite nanoparticles (NP-IL-12) on the apoptosis of ovarian cancer cells. Ovarian cancer cells were treated with medium alone, IL-12 (50 ng/ml), the nanoparticles (NP, 50 μg/ml) alone or NP-IL-12 (50 ng bound IL-12/ml), incubated for 24 h and were then analyzed for cell death using the LDH assay.

6(xi) IL-12-Conjugated Gelatin/Iron Oxide Magnetic Composite Nanoparticles Induce Apoptosis in Human Ovarian Cancer Cells Ovarian cancer cells were treated with medium alone, IL-12 (50 ng/ml), NP (50 µg/ml) or IL-12-conjugated gelatin/iron oxide magnetic composite nanoparticles (NP-IL-12, 50 ng IL-12/ml), incubated for 24 h and were then analyzed for cell death using the LDH assay. As shown in FIG. 18, both IL-12 and NP-IL-12 induced cell death in the cultured cells, as further reflected in the cell morphology.

Example 7

In Vivo Studies: Targeting, Imaging and Apoptosis of Glioma Cells

Materials and Methods

Cell lines and animals. U251 cells were obtained from ATCC (Manassas, Va.) or from the Hermelin Brain Tumor Center (Henry Ford Hospital, Detroit, Mich.). All cells were cultured in DMEM supplemented with 10% FBS (Hyclone, Logan, Utah), 2 mM L-glutamine, and 100 ug/ml streptomycin-penicillin (Invitrogen) at 37° C. under 5% $CO_2$. Female Nu/Nu rats were obtained from NCI Fredericks (Fort Detricks, Md.). All rats were 6-8 weeks old at the time of tumor implantation.

Tumor implantation and nanoparticles administration. Rats were allowed to acclimate for one week after arrival prior to use. Prior to tumor cell implantation, animals were anesthetized and prepared for sterile surgery. A 1 cm long incision was made through the scalp and a 26-gauge needle was used to gently puncture, by twisting, a hole through the skull 2 mm to the right and 2 mm to the dorsal of the midline. The animal was then placed into a stereotaxic device (Kopf, Tujunga, Calif.), equipped with a micro-manipulator and a syringe holder. The needle was lowered 3 mm into the pre-made hole, raised 0.5 mm, and the tumor volume (5 µl) was slowly injected over a total of 2.5 min. The needle was left in place for 1 min and was then slowly raised over 1 min. The animal was removed from the stereotaxic device, the hole sealed with bone wax, the scalp was sutured and the animal was monitored for recovery. On day 4, 7 or 10 after tumor implantation, PBS (10 µl) in absence or presence of control nanoparticles (0.05 mg), TRAIL-conjugated nanoparticles (100 ng TRAIL conjugated to 0.05 mg nanoparticles) or free TRAIL (100, 200 or 800 ng) were implanted in the same manner in the ipsi-lateral or the contra-lateral hemisphere. At either select time points, or at signs of morbidity, standard perfusion with saline by 10% formalin was preformed. The brains were removed and placed in 10% neutral buffered formalin overnight for further processing. For visualization of fluorescently labeled tumors and nanoparticles, at select time points, standard perfusion with saline was preformed. Brains were removed and snap-frozen for sectioning using a cryostat for further visualization.

Histochemistry, immunohistochemistry, nanoparticle visualization and apoptosis detection. Formalin-fixed tissues were embedded in paraffin, sectioned (5 µm), and hematoxylin and eosin (H&E) stained for histomorphological assessment. Hematoxylin stains with blue color the nucleus, the acidic regions of the cytoplasm and the cartilage matrix. Eosin stains with pink color the basic regions of the cytoplasm and the collagen fibers (Gartner and Hiatt, 2001). The 5 µm sections were dried in a 60° C. oven for 1 h and routinely deparafinized to $ddH_2O$. For detection of human cells, sections were incubated with a 1:250 dilution of human mitochondria antibody (Chemicon, cat#H10060). Immunohistochemistry was performed using the Biocare Medical Nemesis 7200 (Concord, Calif.) stainer and reagents. The sections were blocked ith Biocare Sniper block for 7 minutes and incubated with primary antibody in Biocare diluent for 60 min. After buffer rinses, the sections were avidin biotin blocked for 15 min. Following rinses, antigens were detected using universal link, followed by HP (Biocare) and Betazoid DAB. Buffer rinses are then followed by dH2O and 10 second counterstain with CAT Hematoxylin. Control sections were processed omitting the primary antibody.

Gomori's Iron reaction staining (Sheehan and Hrapchak, 1980) for nanoparticle visualization (blue color) was done utilizing 5 μm sections from formalin-fixed paraffin embedded tissue. The 5 μm sections were dried in a 60° C. oven for 1 h and routinely deparanfiinized to ddH$_2$O. For all remaining steps, acid cleaned glassware was used. Slides were immersed in equal parts of 20% HCl and 10% aqueous potassium ferrocyanide for 10-20 minutes. Slides were then rinsed well in ddH$_2$O and counterstained with Nuclear Fast Red for 2 minutes, followed by dehydration, cleared and then cover slipped. Sections of spleen were used as positive controls for each staining.

Staining of apoptotic cells was performed using TUNEL staining (brown staining) that specifically detects apoptotic cells (Shah et al., 2003). Briefly, staining of formalin fixed paraffin embedded tissue was performed utilizing the Apoptag Peroxidase In Situ Apoptosis Detection Kit (Chemicon, Temecula, Calif.) as per manufacturer's instructions. Briefly, 5 μm sections from formalin-fixed paraffin embedded tissue were dried in a 60° C. oven for 1 h and routinely deparafinized. Tissue was then pretreated with proteinase K (20 μg/ml) for 15 mins at room temp. Slides were washed two times in ddH$_2$O and endogenous peroxidase was quenched in 3.0% hydrogen peroxide in PBS for 5 mins at room temperature. Slides were wash twice in PBS and 75 μl/5 cm$^2$ of equilibration buffer was added to each slide for at least 10 seconds. Excess liquid was tapped off and 55 μl/5 cm$^2$ of TdT enzyme was added. Slides were incubated for 1 hour and were then washed in Stop/wash buffer for 15 seconds with agitation, then 10 mins at room temp. Next, the slides were washed in 3 changes of PBS for 1 min each, followed by incubation with 65 μl/5 cm$^2$ anti-digoxigenin conjugate for 30 min. Following 4 changes of PBS for 2 mins each, slides were incubated for 3-6 mins at room temp with 75 μl/5 cm$^2$ peroxidase substrate. Slides were washed for a final 3 changes of ddH$_2$O for 1 min each, incubated in ddH$_2$O for 5 min, and then counterstained with methyl green for 10 mins at room temperature, washed with ddH$_2$O, cleared with 100% n-butanol, dehydrated through xylene and cover slips mounted with permount.

Imaging. Immunohistological and histochemical images were taken at room temperature using a Nikon Eclipse E800M microscope with ×10, X20 and X40 objectives connected to a Nikon DXM1200C digital camera, and digitized using ACT-1C software on Dell Optiplex GX620 computers. Tiff images were imported into Adobe Photoshop for composite production. Insets are magnifications performed using Photoshop.

Fluorescent images were taken at room temperature using a Nikon Cl confocal microscope with ×4, X10 and X20 objectives connected to a digital camera. Bitmap images were imported into Adobe Photoshop for composite production.

In vivo MR imaging studies: An appropriate state of anesthesia was obtained with halothane (3% for induction, 0.7% to 1.5% for maintenance in a 2:1 mixture of N$_2$:O$_2$). The anesthetized rats were placed in a 7 Tesla, 20 cm bore superconducting magnet (Magnex Scientific, Abingdon, England) interfaced to a BRUKER console (Bellerica, Mass.). A 12 cm self-shielded gradient set with maximum gradients of 45 gauss/cm was used. The radio frequency (RF) pulses were applied by a 7.5 cm diameter saddle coil actively decoupled by TTL control from the 3.2 cm diameter surface receive coil which was positioned over the center line of the animal skull. Stereotaxic ear bars was used to minimize movement during the imaging procedure. Rectal temperature was maintained at 37±0.5° C. using a feedback controlled water bath. A modified fast low angle shot (FLASH) imaging sequence was employed for reproducible positioning of the animal in the magnet at each MRI session. MR studies were performed using T1-, T2- and T2*-weighted MRI scans. For detection of iron oxide labeled cells, scans typically employed are T2*W gradient echoes. Average examination times for the T1-, T2- and T2*-weighted MRI scans were approximately 9, 13 and 13 minutes, respectively, for in vivo studies of brain tumors. The following parameters were used to acquire MRI: T1-weighted multislice sequence (TR/TE=500/10 ms, 128× 128 matrix, 13-15 slices, 1 mm thick, 32 mm field of view (FOV), number of excitation (NEX)=4). T2 weighted images were obtained using standard two-dimensional Fourier transformation (2DTF) multislice (13-15) multiecho (6 echoes) MRI. A series of six sets of images (13-15 slices for each set) were obtained using TEs of 10, 20, 30, 40, 50 and 60 msec and a TR of 3000 msec. The images were produced using 32 mm FOV, 1 mm slice thickness, 128×128 matrix, and NEX=2. T2* weighted images were obtained using standard multislice (13-15 slices) multi gradient echo (6 echoes) MRI. A series of six sets of images (13-15 slices for each set) were obtained using TEs of 5, 10, 15, 20, 25 and 30 msec and a TR of 3000 msec. The images were produced using 32 mm FOV, 1 mm slice thickness, 128×128 matrix and NEX=2. Both the T2 and T2* images were used to measure the T2 and T2* maps. Three dimensional (3D) gradient echo MR images were obtained with TR=100 msec, TE=6 msec, 10° of flip angle (FA), 32×32×16 mm$^3$ FOV, 256×192×64 matrix, and NEX=1. The total time for entire sequence was approximately 20 minutes. To maintain the body temperature, heating pad was used. Rectal probe were used to monitor the body temperature. To compare the image quality between the 3 tesla and 7 tesla MR systems, randomly selected animals underwent MRI using 3 tesla. For imaging with 3 tesla MRI, appropriate anesthesia was obtained by injecting ketamine chloride and xylazine. Rats were properly rapped with heated drapes to maintain body temperature.

7(i) Establishment of Glioma Animal Models

In order to examine the in vivo effect of TRAIL-conjugated gelatin/iron oxide magnetic composite nanoparticles (NP-TRAIL), two glioma animal models were established. In the first model, human U87 or U251 cells were intracranially implanted into nude mice. In the second model, we employed human glioma cells from fresh operative tumor samples were implanted in nude rats, generating tumors that maintain the original properties of the original tumors, thus providing a system that can predict the response of these tumors to different anti-cancer treatments.

Figure 19:
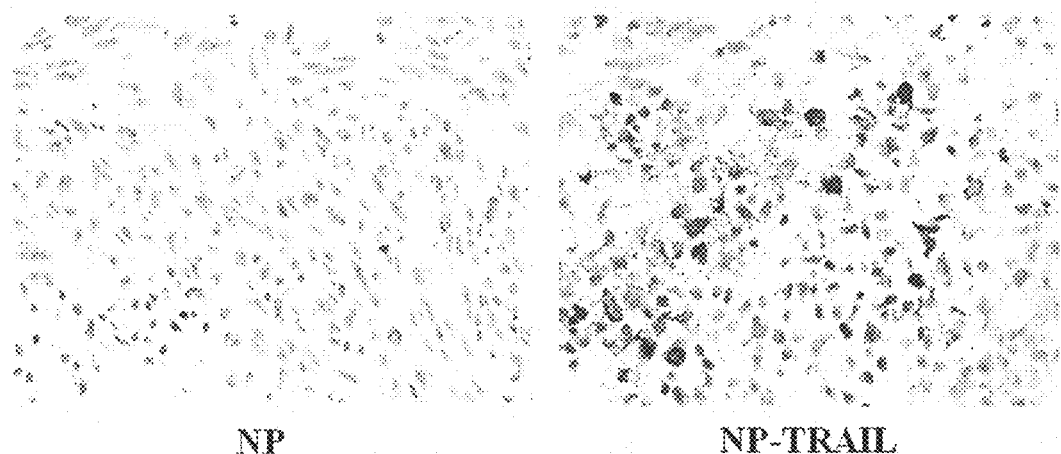
FIG. 19 shows tumor sections from rats treated with either TRAIL-conjugated gelatin/iron oxide magnetic composite nanoparticles (NP-TRAIL) or the nanoparticles (NP) alone. Human U251 glioma cells were employed as xenografts in rat brains and tumors were allowed to develop for 7 days at which time either NP or NP-TRAIL were intracranially injected at the site of the tumor. The degree of cell apoptosis in tumors of control rats treated with PBS (not shown), NP or NP-TRAIL were examined 7 days after treatment, and cell apoptosis was determined using TUNEL staining (brown staining), which specifically detects apoptotic cells.

7(ii) TRAIL-Conjugated Gelatin/Iron Oxide Magnetic Composite Nanoparticles Induce Cell Apoptosis in Glioma In order to examine the effect of NP-TRAIL in vivo, human U251 glioma cells were employed as xenografts. Tumors were allowed to develop for 7 days at which time NP-TRAIL, gelatin/iron oxide magnetic composite nanoparticles (NP) alone or PBS were intracranially injected at the site of the tumor. The degree of cell apoptosis was examined after 7 days of treatment. Cell apoptosis was determined using TUNEL staining (brown staining) that specifically detects apoptotic cells. FIG. 19 shows tumor sections from rats treated with either NP alone or NP-TRAIL. As shown, NP alone did not induce a significant degree of cell apoptosis; however, NP-TRAIL induced a large degree of cell apoptosis as determined by TUNEL (brown staining)-positive cells. In the PBS-treated rats, no significant cell apoptosis was indicated as well (data not shown).

Figure 20:
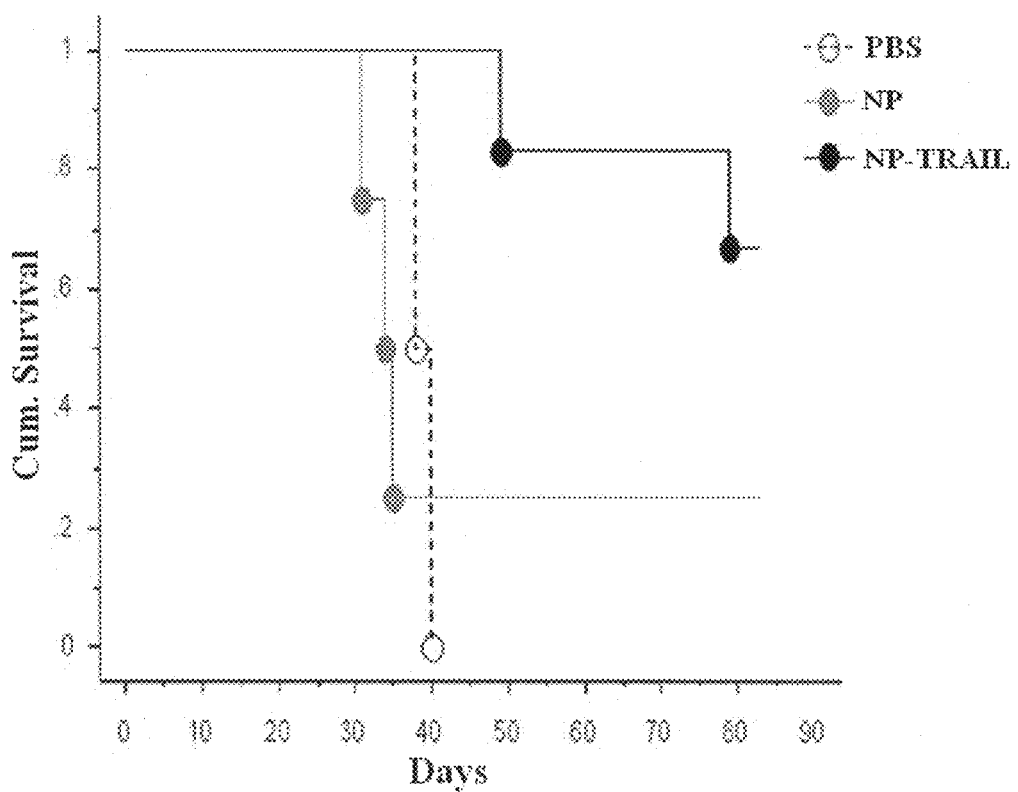
FIG. 20 shows the effect of TRAIL-conjugated gelatin/iron oxide magnetic composite nanoparticles (NP-TRAIL) on survival of human U251 implanted rats. The nanoparticles (NP) alone, NP-TRAIL or PBS were injected directly into the tumor 7 days post tumor cell implantation, and animals were observed for signs of distress and/or morbidity and were euthanized at that time.
Figure 21A:
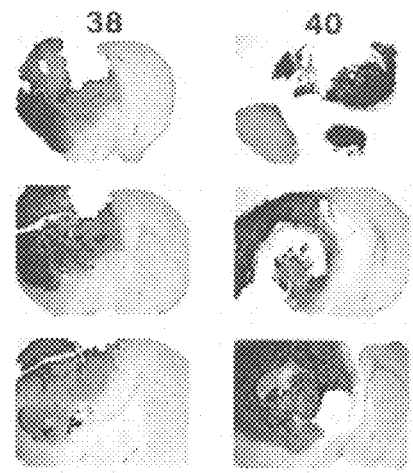
FIGS. 21A-21C show the effect of TRAIL-conjugated gelatin/iron oxide magnetic composite nanoparticles (NP-TRAIL) (21C) vs. the nanoparticles (NP) alone (21B) or PBS (21A) administration on tumor volume at time of morbidity. Rats were perfused with formalin at time of euthanasia, brains were harvested and H&E staining was performed. Representative tumor volume slices are shown. Number above series of pictures represents the day of euthanasia.
Figure 21B:
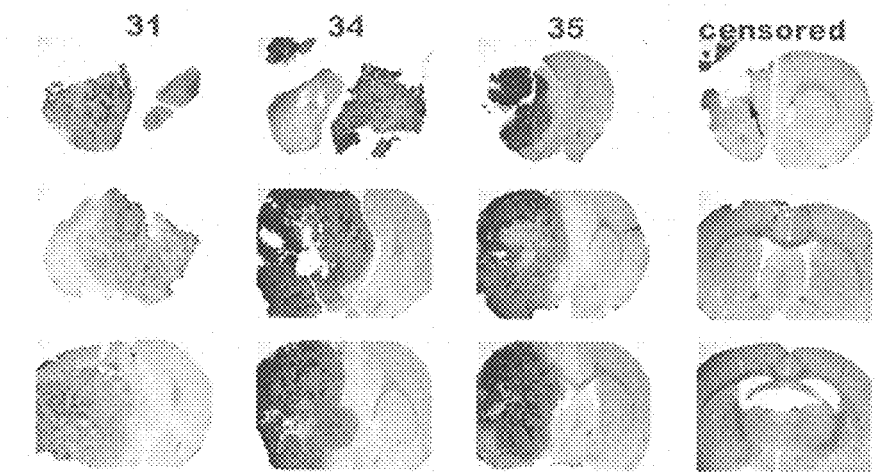
Figure 21C:
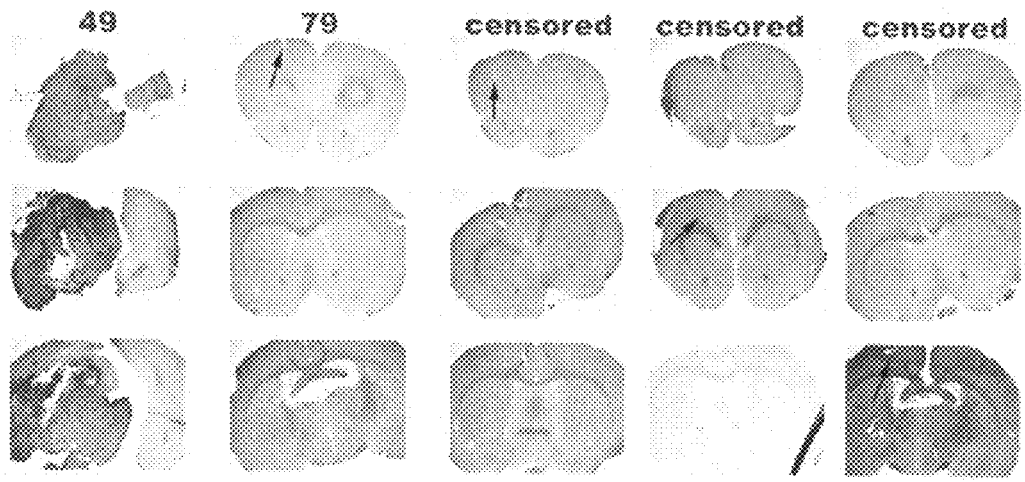

7(iii) TRAIL-Conjugated Gelatin/Iron Oxide Magnetic Composite Nanoparticles Prolong Survival in Glioma In order to determine whether NP-TRAIL (100 ng TRAIL) could provide a survival benefit, PBS, NP alone or NP-TRAIL were delivered intratumoraly directly into xenogenic human U251 tumors in the brains of nude rats. Animals were then monitored for signs of morbidity and euthanized at the appearance of any signs or at day 85 post tumor implant. As shown in FIG. 20, treatment with NP-TRAIL significantly prolonged survival over that of NP alone (p=0.0248) or PBS (p=0.0288). Photomicrographs of representative tumors at time of morbidity are shown in FIGS. 21A-21C. Large tumors are evident in animals euthanized due to tumor morbidity, but no tumors are evident in censored animals. Some scaring is evident in these animals however (arrows). Each series is taken from the same animal and from sections 2 mm apart. A similar experiment was also accomplished with sTRAIL substituting the injected 10 μl PBS containing NP-TRAIL (100 ng TRAIL) for 100, 200 and 800 ng sTRAIL. These experiments indicated similar survival results to that observed with PBS. However, the experiment with the higher concentration of sTRAIL indicated some damage to oligodendrocytes.

Figure 22:
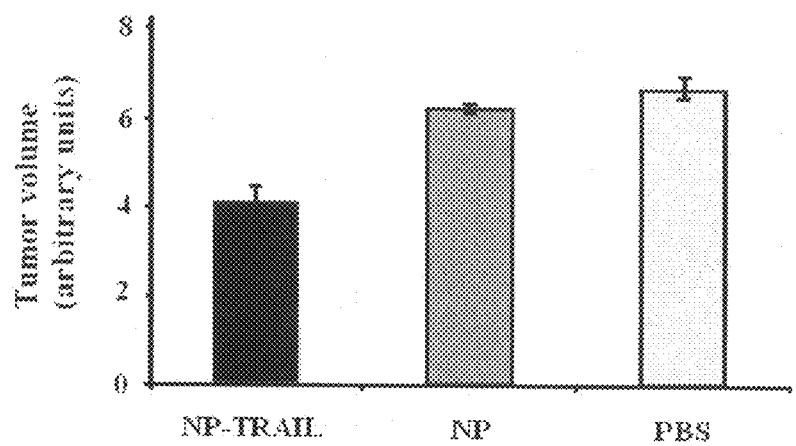
FIG. 22 shows that TRAIL-conjugated gelatin/iron oxide magnetic composite nanoparticles (NP-TRAIL) administration leads to a decrease in overall tumor burden as compared with the nanoparticles (NP) alone or PBS administration. Rats were intracranially implanted with human U251 cells and after 7 days, NP-TRAIL, NP or PBS were administered. Animals were euthanized at day 21, and brain tissue was harvested and sectioned for volume determination. Slides were photodocumented with identical settings for all slides used in this determination. Volume was determined by measuring greatest width and length of tumor for every $15^{th}$ 5 μm slice. Volume for each slice is determined and multiplied by the number of slices to the next measured slice until edge of tumor is achieved.

7(iv) TRAIL-Conjugated Gelatin/Iron Oxide Magnetic Composite Nanoparticles Decrease Tumor Volume in Glioma In order to determine the effect of NP-TRAIL on tumor burden, PBS, NP alone or NP-TRAIL were delivered intratumoraly into xenogenic human U251 tumors in the brains of nude rats. Animals were euthanized on day 21 post tumor implant and brains were harvested for sectioning and H&E staining. Brains were cut into 2 mm blocks, processed, and blocks with evident tumor were cut in 5 um sections, with every $15^{th}$ section kept and stained with H&E, and tumor volume on this slide determined. Max width and height of tumor on each $15^{th}$ slide was measured, and total tumor burden determined by multiplying max W×H×(5×15) for each slide with evident tumor and these numbers added. Statistical significance was determined with Statview using Fischer's PLSD (significance level 5%). As shown in FIG. 22, NP-TRAIL administration significantly decreased tumor burden as compared with NP alone or PBS. No significant difference was seen between NP alone and PBS administration.

7(v) Tumor Tracking Ability

Figure 23:
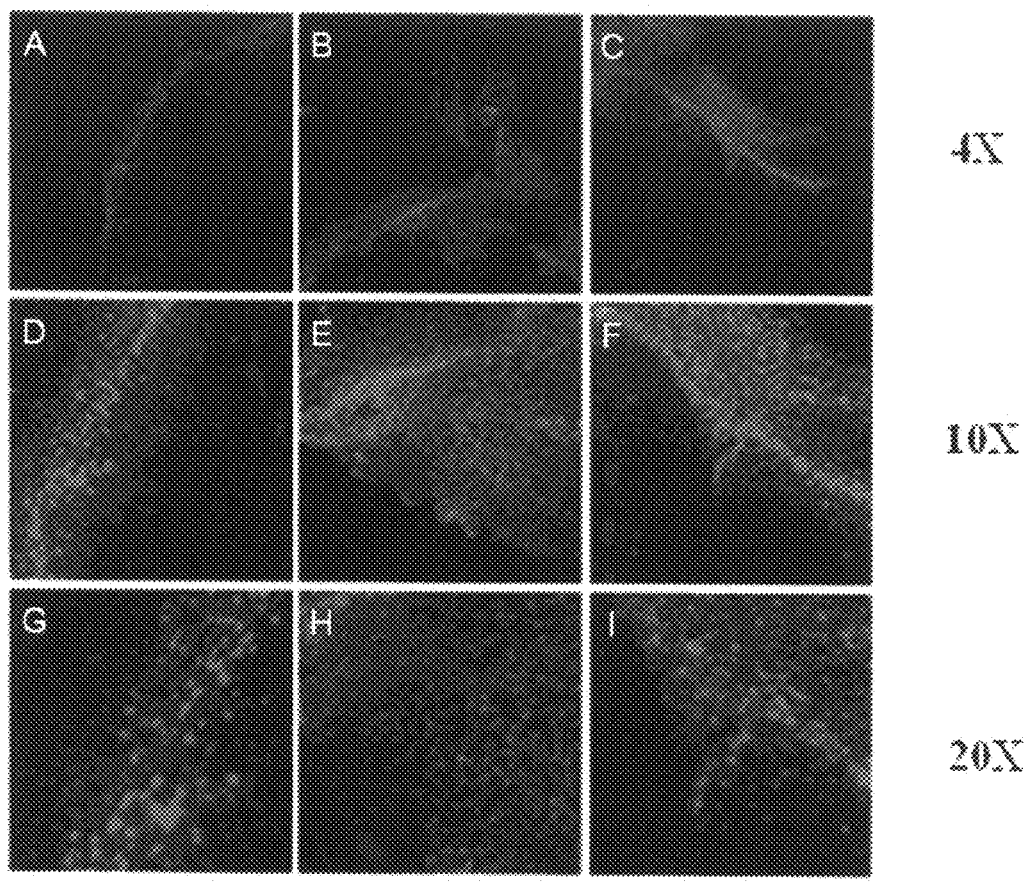
FIG. 23 shows the ability of gelatin/iron oxide magnetic composite nanoparticles (NP) to track to sites of tumor growth. Rhodamine-labeled NP (NPR) were implanted in the contralateral hemisphere of rat brains 7 days after U251 tumor cell implantation. Four days later, animals were euthanized, and brains were harvested and snap frozen for sectioning and imaging. Panels A, D and G show images of NPR in the corpus collosum part close to the site of the NPR injection; panels B, E and H shows the site of NPR implantation; and panels C, F and I show images of NPR in the corpus collosum part close to the site of tumor cells. Magnification 4× (panels A, B, C); 10× (panels D, E, F); and 20× (panels G, H, I).

The ability of NP to travel from the site of implantation to the site of tumor growth is a useful therapeutic potential of NP, particularly for brain tumor therapy. Thus, in order to determine that ability, U251 tumor cells were implanted into the left hemisphere of nude rat brains on day 0 and rhodamine-labeled gelatin/iron oxide magnetic composite nanoparticles (NPR) were administered parallel to the tumor implantation but in the contralateral hemisphere 7 days later. On day 11 (4 days post NPR administration), animals were euthanized and perfused with saline, and brains were removed and snap frozen for cryosectioning and analysis with confocal microscopy. As shown in FIG. 23, NPR are easily seen tracking along the corpus collosum. Although some NPR are indeed migrating away from the tumor mass, the majority of NPR were seen to be migrating towards the tumor mass in the left hemisphere. Similar behavior was observed for rhodamine-labeled TRAIL-conjugated gelatin/iron oxide magnetic composite nanoparticles (NPR-TRAIL).

7(vi) Tumor Destruction

Figure 24:
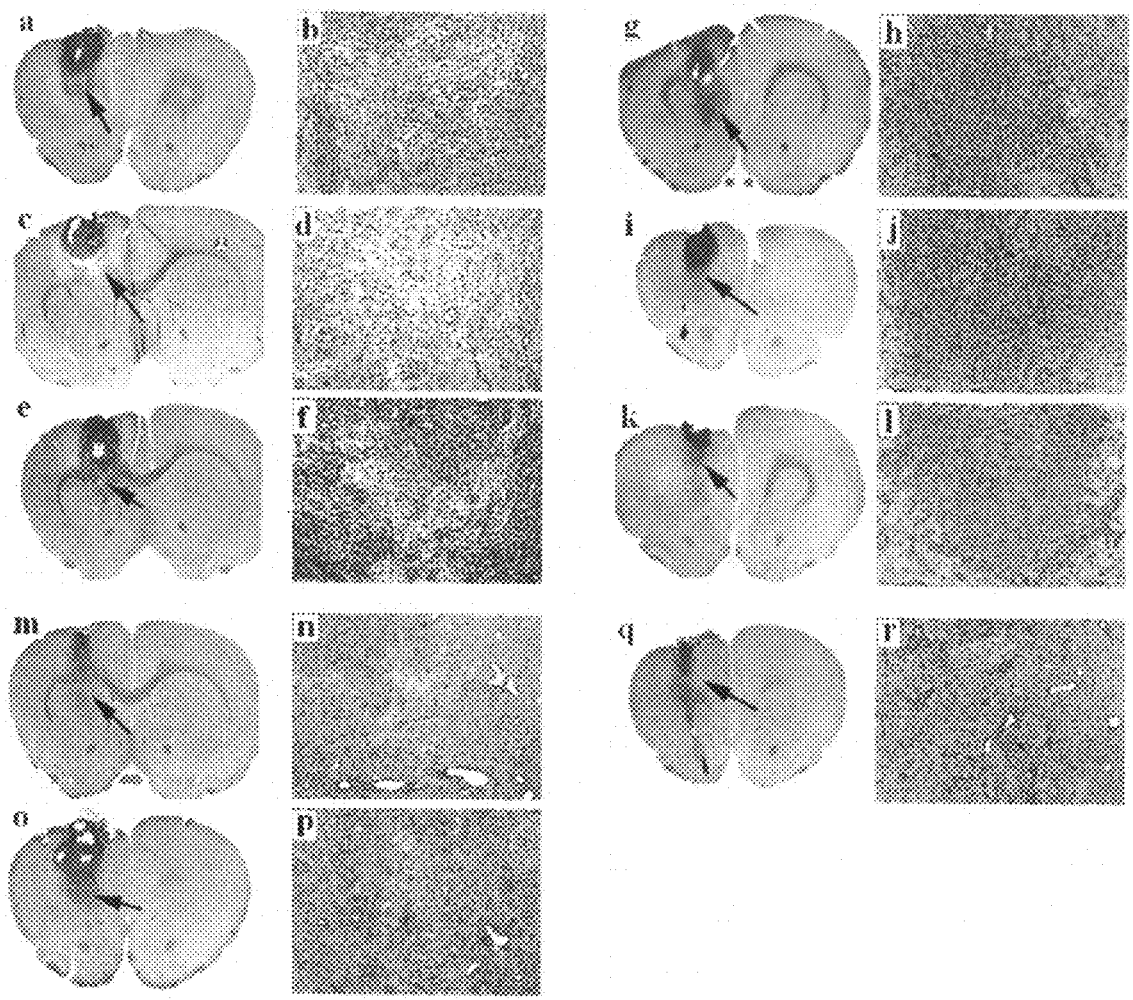
FIG. 24 shows that TRAIL-conjugated gelatin/iron oxide magnetic composite nanoparticles (NP-TRAIL) administration leads to large areas of tissue destruction, specifically demonstrated in panels b, d and f, which is not seen neither with nanoparticles (NP) alone nor with PBS administration. Nude rats were implanted with U251n tumors on day 0; NP-TRAIL, NP alone or PBS were intraneoplastically administered on day 7; and animals were euthanized and tissue was harvested on day 14. NP-TRAIL (panels a-f); NP (panels g-l); PBS (panels m-r). Magnification 1× (panels a, c, e, g, i, k, m, o, q); 10× (panels b, d, f, h, j, l, n, r). Arrows indicate the lower part of the tumor mass.
Figure 25:
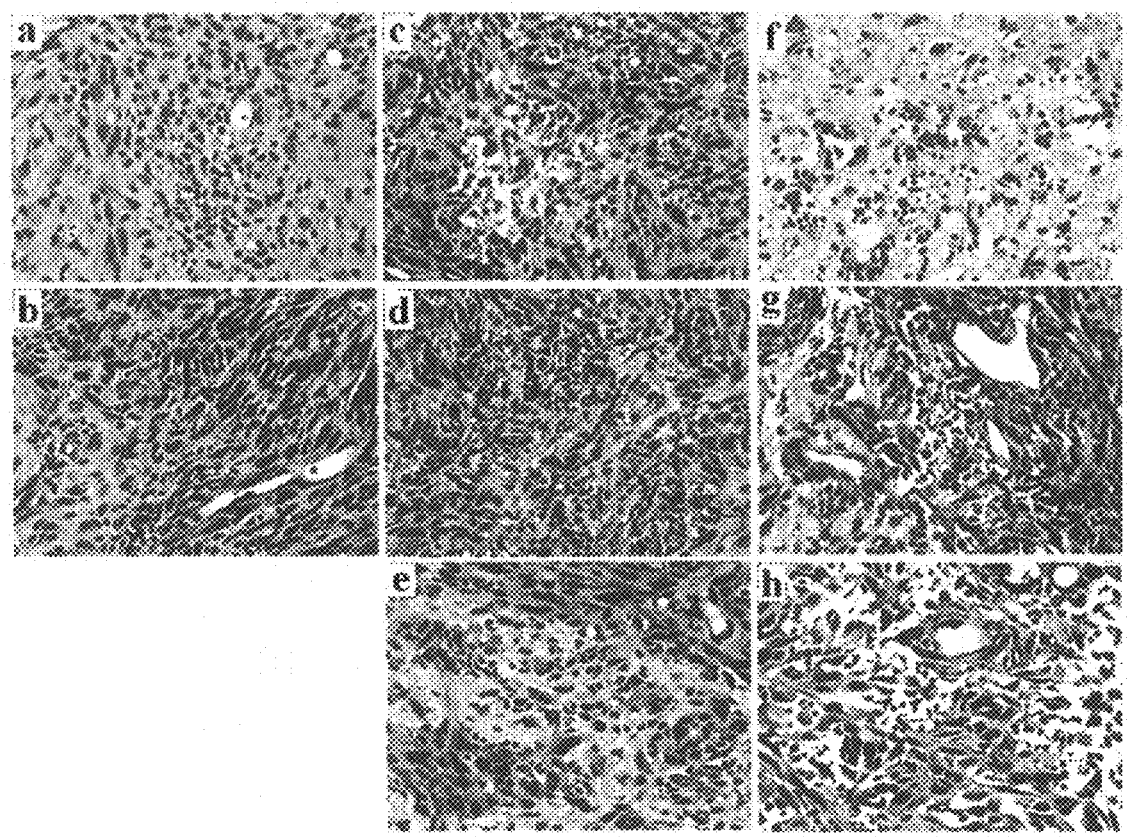
FIG. 25 shows increased tumor cell destruction in rats receiving TRAIL-conjugated gelatin/iron oxide magnetic composite nanoparticles (NP-TRAIL) vs. the nanoparticles (NP) or PBS only. Animals were implanted with human U251n cells on day 0 and were administered with PBS, NP or NP-TRAIL on day 7. Animals were euthanized on day 14 and brain tissue processed and hemotoxylin and eosin stained. PBS (panels a-b); NP (panels c-e); NP-TRAIL (panels f-h). Magnification 40×.

In this experiment, the ability of NP-TRAIL to destruct the tumor was determined. In particular, nude rats were implanted with U251n tumors on day 0. NP-TRAIL, NP alone or PBS were intraneoplastically administered on day 7, and animals were euthanized and tissue harvested on day 14. As shown in FIG. 24, NP-TRAIL administration led to the development of large areas of tumor destruction in the lower part of the tumor mass, which were not seen in NP alone- or PBS-administered animals. Many necrotic and apoptotic cells were seen within this area (right panels) following NP-TRAIL administration; however were not seen following NP or PBS administration. FIG. 25 demonstrates high magnification of the areas of tumor destruction following therapy.

Figure 26A:
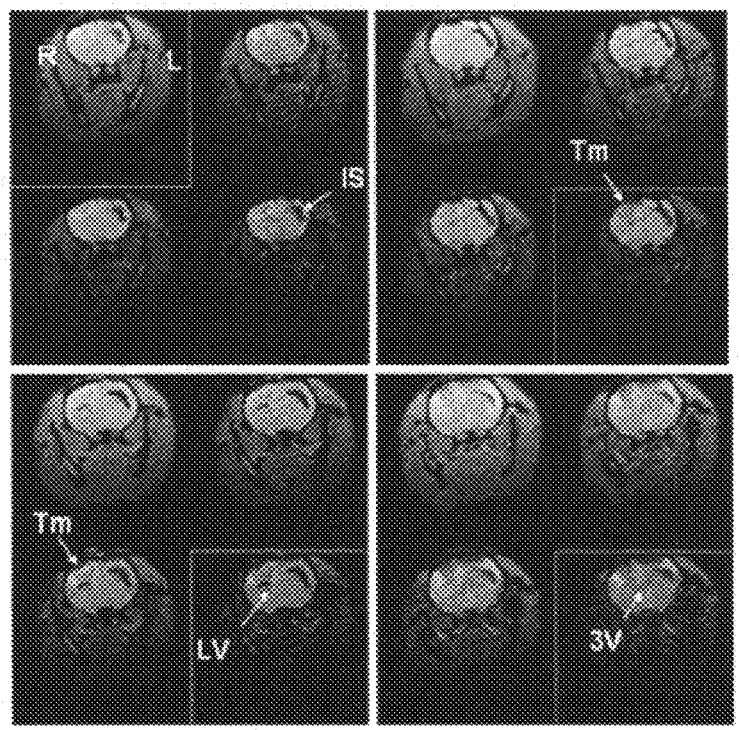
FIGS. 26A-26B show that TRAIL-conjugated gelatin/iron oxide magnetic composite nanoparticles (NP-TRAIL) (26B) induce lower signal intensity both at the margin and inside the tumor, compared with the nanoparticles (NP) alone (26A), as shown by MRI, indicating that NP-TRAIL arrive at the borders and inside human glioma xenograft implanted within nude rats. U251n human glioma cells were implanted in nude rats, and NP or NP-TRAIL were intracranially injected in the contra lateral side of the tumor 11 days later. MR images were obtained 8 days later. Each figure shows 4 consecutive sections of MRI, each section has 4 images with different echo time (TE). Longer TE (right lower image in small box). More signal intensity loss (black) due to iron. R-right; L-left; IS-injection site (left); Tm-Tumor (right); LV-lateral ventricle; and 3V-$3^{rd}$ ventricle.
Figure 26B:
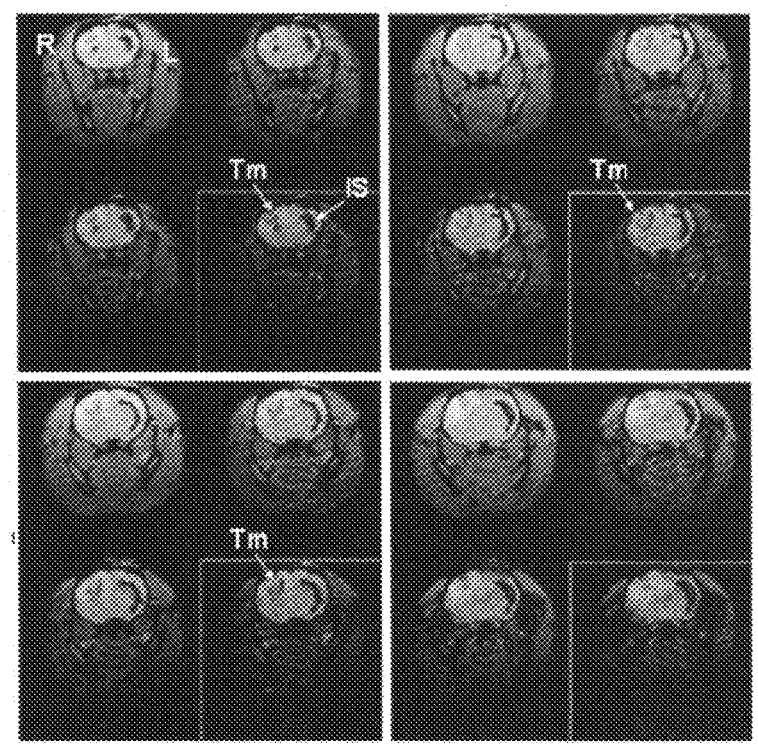

7(vii) TRAIL-Conjugated Gelatin/Iron Oxide Magnetic Composite Nanoparticles Arrive at the Borders and Inside Human Glioma Xenograft Implanted within Nude Rats as Shown by MRI U251n human glioma cells were implanted in nude rats and 11 days later, NP or NP-TRAIL were intracranially injected in the contra lateral side of the tumor. MR images were obtained 8 days later. As shown in FIGS. 26A-26B, NP-TRAIL (26B) induced lower signal intensity both at the margin and inside the tumor, compared to NP only (26A). The lower intensity implies the presence of nanoparticles.

Figure 27:
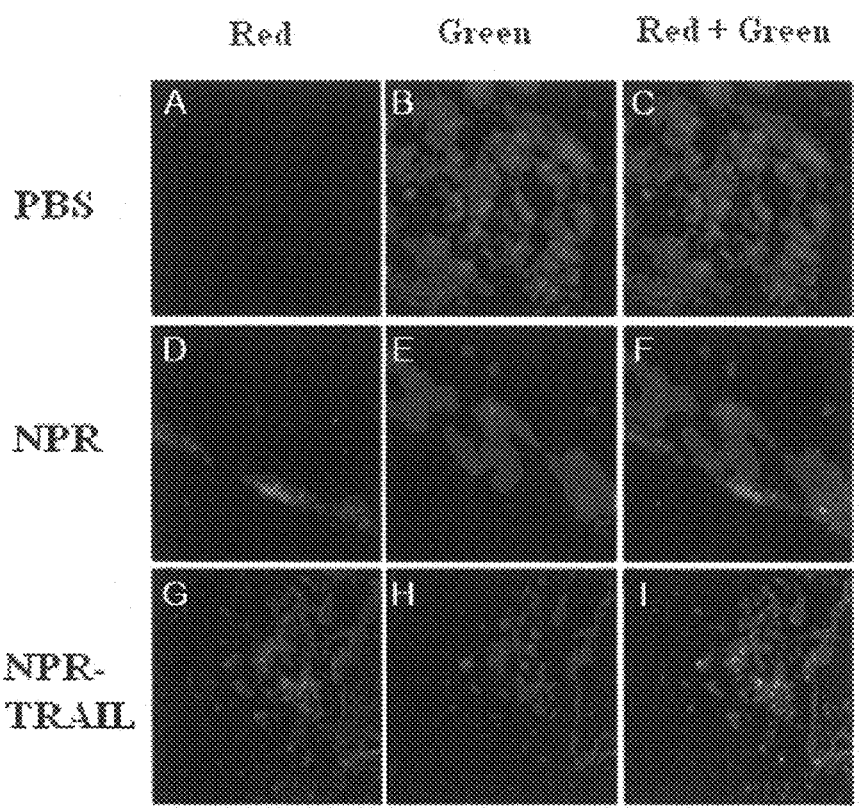
FIG. 27 shows the ability of TRAIL-conjugated rhodamine-labeled gelatin/iron oxide magnetic composite nanoparticles (NPR-TRAIL) to be taken up by tumor cells in vivo. Rhodamine-labeled gelatin/iron oxide magnetic composite nanoparticles (NPR) alone or NPR-TRAIL were implanted directly within the tumor mass 7 days after GFP-U251 tumor cells implantation. Four days later, animals were euthanized, and brains were harvested and snap frozen for sectioning and imaging (red color and green color indicate the presence of NPR and GFP-U251 tumor cells, respectively). As shown in the panel G,H and I, NPR-TRAIL are not only found in areas of tumor mass but also colocalized with tumor cells (panel I). However, NPR alone are found in areas of tumor mass but are not colocalized with tumor cells (panels D, E and particularly F). Control animals were treated with PBS.

7(viii) In Vivo Uptake of TRAIL-Conjugated Rhodamine-Labeled Gelatin/Iron Oxide Magnetic Composite Nanoparticles by Tumor Cells NPR alone or NPR-TRAIL were implanted directly within the tumor mass 7 days after GFP-U251 tumor cells implantation. Four days later, animals were euthanized, and brains were harvested and snap frozen for sectioning and imaging (red color and green color indicate the presence of NPR and GFP-U251 tumor cells, respectively). As shown in FIG. 27, whereas NPR alone were found in areas around tumor cells but were not colocalized with tumor cells (panels D, E, F), NPR-TRAIL were found in areas of tumor destruction colocalized with tumor cells (panels G, H, I). It is further shown that the tumor visible in the NPR-TRAIL-treated animal is degraded compared to the tumor visible in both the PBS- or NPR-treated-animals, with only a few viable tumor cells clearly visible in this section. This experiment indicates that TRAIL led to tumor cell uptake of NP, as shown in vitro in Example 6(v).

Figure 28:
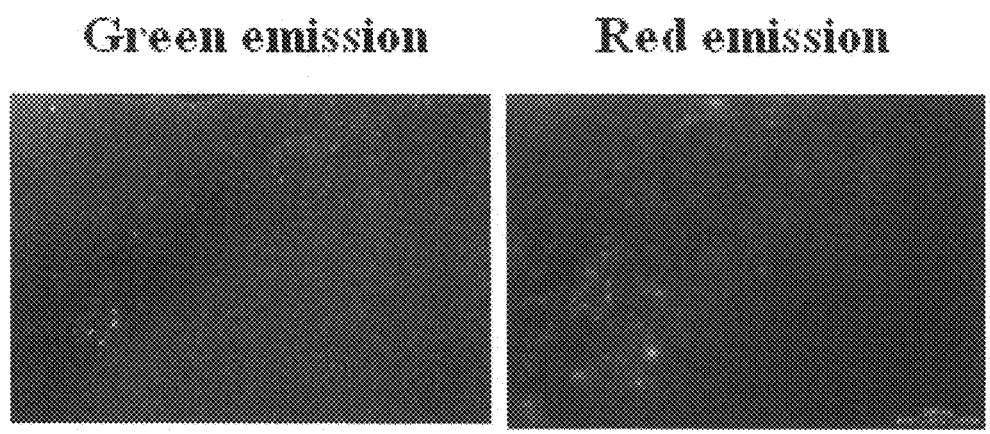
FIG. 28 shows that cRGD peptide-conjugated rhodamine-labeled gelatin/iron oxide magnetic composite nanoparticles (NPR-cRGD) migrate towards tumor cells in vivo. NPR-cRGD (10 μl containing 0.05 mg nanoparticles bound to about 2 μg cRGD peptide) were injected to the contra-lateral side of the nude rat brains 7 days after GFP-U251 tumor cells implantation. Four days later animals were euthanized, and brains were harvested and snap frozen for sectioning and imaging (red color and green color indicate the presence of rhodamine-labeled gelatin/iron oxide magnetic composite nanoparticles (NPR) and GFP-U251 tumor cells, respectively).

7(ix) Migration of cRGD Peptide-Conjugated Rhodamine-Labeled Gelatin/Iron Oxide Magnetic Composite Nanoparticles to Gliomas cRGD peptide-conjugated rhodamine-labeled gelatin/iron oxide magnetic composite nanoparticles (NPR-cRGD, 10 μl containing 0.05 mg nanoparticles conjugated to about 2 μg cRGD peptide) were injected to the contra-lateral side of the brain, 7 days after GFP-U251 tumor cells implantation. Four days later, animals were euthanized, and brains were harvested and snap frozen for sectioning and imaging (red color and green color indicate the presence of NPR and GFP-U251 tumor cells, respectively). FIG. 28 shows that NPR-cRGD migrated to the tumor site.

Figure 29:
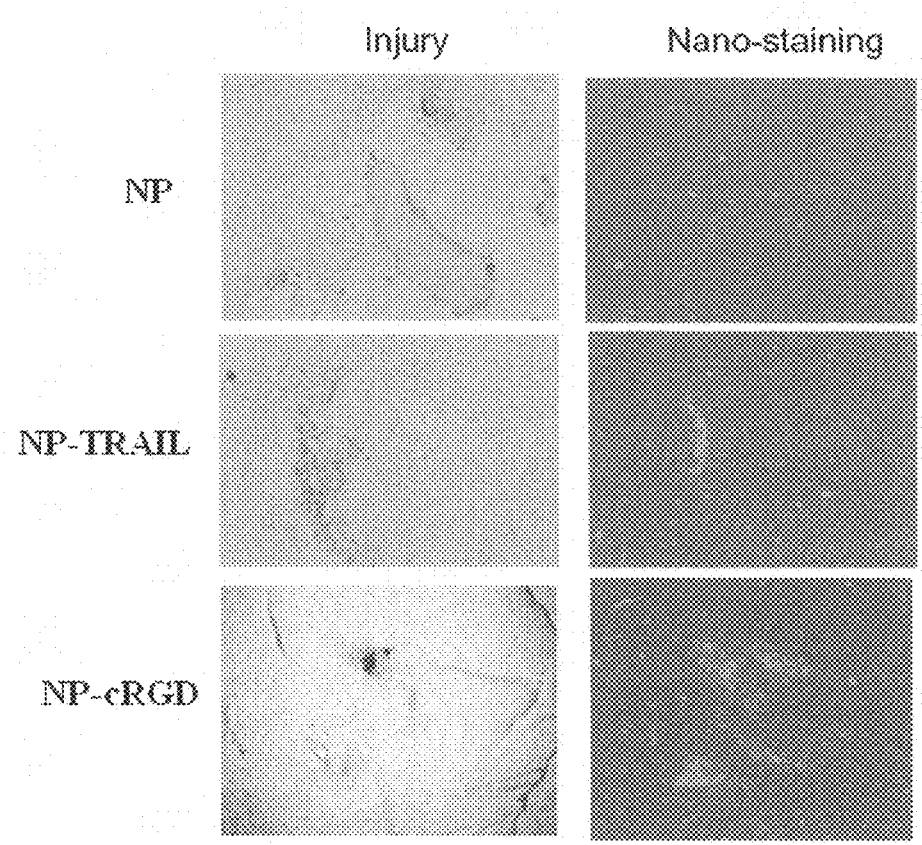
FIG. 29 shows that both cRGD peptide-conjugated rhodamine-labeled gelatin/iron oxide magnetic composite nanoparticles (NPR-cRGD) and TRAIL-conjugated rhodamine-labeled gelatin/iron oxide magnetic composite nanoparticles (NPR-TRAIL) migrate towards injury site in vivo. Injury was induced by needle injection of PBS at the left side of the brain, and following 4 days, 5 μl (25 μg) of rhodamine-labeled gelatin/iron oxide magnetic composite nanoparticles (NPR) alone, NPR-TRAIL (50 ng bound TRAIL) and NPR-cRGD were injected to the contra-lateral side of the brain. After 4 days, the animals were sacrificed and the fluorescence of the NPR was visualized under fluorescent microscope. As shown, few NPR were present at the other side of the brain but their distribution was abundant. NPR-TRAIL were localized mainly along the site of injury. In contrast, the NPR-cRGD were distributed all over the side of the injured brain and also along the corpus callosum.

7(x) Migration of cRGD Peptide- and TRAIL-Conjugated Rhodamine-Labeled Gelatin/Iron Oxide Magnetic Composite Nanoparticles Toward Injury Site Injury was induced by needle injection of PBS at the left side of the brain. Following 4 days, 5 μl (25 μg) of NPR alone, NPR-TRAIL (50 ng TRAIL) and NPR-cRGD were injected to the contra-lateral side of the brain. After 4 days, the animals were sacrificed and the fluorescence of the NPR was visualized under fluorescent microscope. As shown in FIG. 29, few NPR were present at the other side of the brain but their distribution was abundant. NPR-TRAIL were localized mainly along the site of injury. In contrast, NPR-cRGD were distributed all over the side of the injured brain and also along the corpus callosum. These results suggest that the nanoparticles have some ability to track to site of injury and that NPR-TRAIL show selective accumulation in the site of injury. NPR-cRGD have tracking ability but their distribution is not limited to the site of injury and they may bind to inflammatory cells that accumulate there as well. These results have important implications for the use of the NP system to deliver drugs in brain injury, stroke and inflammatory diseases in the brain.

Example 8

The Cytotoxic Effects of TRAIL-Conjugated Gelatin/Iron Oxide Magnetic Composite Nanoparticles on Bladder Carcinoma Cells, Breast Cancer Cells and Normal Breast Cells In these experiments, the cytotoxic effects of TRAIL-conjugated gelatin/iron oxide magnetic composite nanoparticles (NP-TRAIL) on various cancer cells other than glioma cells were determined. The cancer cell lines particularly used were the bladder carcinoma cells TSU-PR1 and the breast cancer cells MDA-MB, and the normal breast cells MCF10A were used as controls. In addition, the effect on these cells of NP-TRAIL in combination with proteasome inhibitor (PS), a multicatalytic proteinase complex responsible for the majority of intracellular protein degradation, was studied. Pharmacologic inhibitors of the proteasome possess in vitro and in vivo antitumor activity. Preclinical studies demonstrate that proteasome inhibition potentiates the activity of other cancer therapeutics such as TRAIL in part by down regulating chemoresistance pathways.

Cells ($1 \times 10^5$/well) were treated with different concentrations of TRAIL (10-100 ng/ml), NP or NP-TRAIL (10-40 ng TRAIL/ml), in the absence or presence of PS (5 mM). Cell death was determined after 24 h using LDH assay. 100% cell death was determined in Triton X-100-treated cells and data normalized.

Figure 30A:
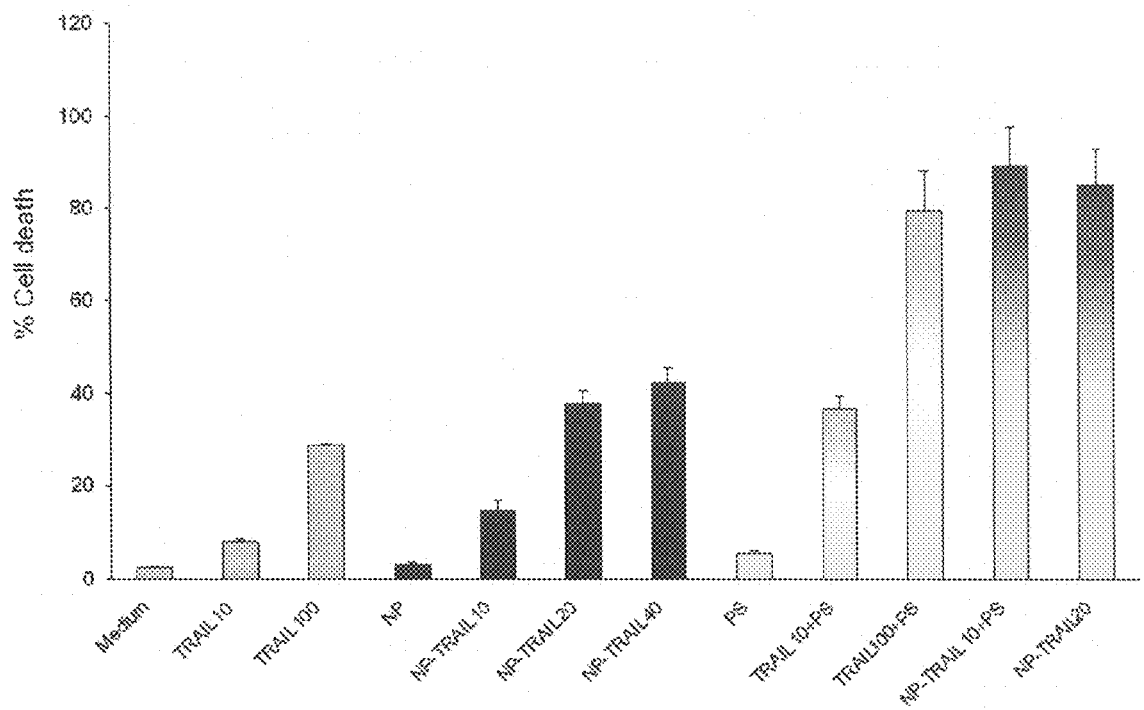

As shown in FIG. 30A-30B, normal breast cells MCF10A did not respond to all of the treatments described above, indicating that these treatments are non-toxic to normal cells. As further shown, the activity of NP-TRAIL was potentiated after treatment with PS. This finding may be of high significance, in particular when planning effective treatment strategies.

REFERENCES

Ashkenazi A., Pai R. C., Fong S., Leung S., Lawrence D. A., Marsters S. A., Blackie C., Chang L., McMurtrey A. E., Hebert A., DeForge L., Koumenis I. L., Lewis D., Harris L., Bussiere J., Koeppen H., Shahokh Z., Schwall R. H., *J. Clin. Invest.*, 1999, 104, 155-162
Blass M., Kronfeld I., Kazimirsky G., Blumberg P. M., Brodie C., *Mol. Cell. Biol.*, 2002, 22, 182-195
Bockstaller M., Lapetnikov Y., Margel S., Thomas E. L., *J.A.C.S.*, 2003, 125, 5276
Bunker B. C., Rieke P. C., Tarasevich B. J., Campbell A. A., Fryxell G. E., Graff G. L., Song L., Liu J., Virden J. W., McVay G. L., *Science*, 1994, 264, 48
Carlo-Stella C., Lavezza C., Locatelli A., Vigano L., Gianni A. M., Gianni L., *Clin Cancer Res.*, 2007, 13, 2313-2317
Denicourt C., Dowdy S. F., *Science*, 2004, 305, 1411
Desjardins A., Rich J. N., Quinn J. A., Vredenburgh J., Gururangan S., Sathornsumetee S., Reardon D. A., Friedman A. H., Bigner D. D., Friedman H. S., *Front. Biosci.*, 2005, 10, 2645-2668
Galperin A., Margel D., Baniel J., Dank G., Biton H., Margel S., *Biomaterials*, 2007, 28, 4461-4468
Gartner L. P., Hiatt J. L., *Color textbook of histology*, $2^{nd}$ Edition, 2001, 2-3
Giese A., Bjerkvig R., Berens M. E., Westphal M., *J Clin Oncol.*, 2003, 21, 1624-1636
Gozuacik D., Kimchi A., *Oncogene*, 2004, 23, 2891-2906
Green-Sadan T., Kuttner T., Lublin T., Kinor N., Boguslavsky Y., Margel S., Yadid G., *Experimental Neurology*, 2005, 194, 97
Hergt R., Hiergeist R., Hilger I., Kaiser W. A., Margel S., Richter U., *J. of Magnetism & Magnetic Materials*, 2004, 270, 345-357
Lacoste J., Vaillant D., Carlsson D. J., *J. Polm. Sci., Part A: Polym. Chem.*, 1993, 31, 715
Leemputten E. V., Horisberger M., *Biotech. and Bioeng.*, 1974, 16, 997
Margel S. et al., Microspheres, Microcapsules & Liposomes, Ed. R. Arshady, Citus Ltd, London, 1999, 2, 11-42
Melamed O., and Margel S., *J. of Colloid & Interface Sci.*, 2001, 241, 357-365
Riccardi C., Nicoletti I., *Nature Protocols*, 2006, 1, 1458-1461
Sanson M., Thillet J., Hoang-Xuan K., *Curr Opin Oncol.*, 2004, 16, 607-613
Shah K., Tang Y., Breakefield X., Weissleder R., *Oncogene*, 2003, 22, 6865-6872
Shankar S., Srivastava R. K., *Drug Resistance Updates*, 2004, 7, 139-156
Sheehan D. C., Hrapchak B. B., Theory and Practice of Histotechnology, $2^{nd}$ Edition, The C.V. Mosby Company, 1980
Shir A., Levitzki A., *Cell Mol Neurobiol.*, 2001, 21, 645
Smyth M. J., Takeda K., Hayakawa Y., Peschon J. J., Van Den Brink M. R. M., Yagita H., *Immunity*, 2003, 18, 1-6
Szymonifka M. J., Chapman K. T., *Tetrahedron Letters*, 1995, 36, 1597
Van Meir E. G., Bellail A., Phuphanich S., *Semin Oncol.*, 2004, 31, 38
Wang S., El-Deiry W, F., *Oncogene*, 2003, 22, 8628-8633
Wei Lu, Qing Sun, Jin Wan, Xin-Guo Jiang, *Cancer Res.*, 2006, 66, 11878-11887
Zhang Y., Lee H. J., Boado R. J., Pardridge W. M., *The J. Of Gene Medicine*, 2002, 4, 183-194

The invention claimed is:

1. A nanoparticle comprising: a metal chelating polymer core, and a magnetic metal oxide coating, said magnetic metal oxide coating coats said metal chelating polymer core, and TNF-related apoptosis-inducing ligand (Apo-2L), covalently bound to said metal chelating polymer core, wherein covalently includes binding via an amino group of said metal chelating polymer and an amino group of said TNF-related apoptosis-inducing ligand.

2. The nanoparticle of claim 1, wherein said magnetic metal oxide is an iron oxide or a ferrite derived from an iron oxide.

3. The nanoparticle of claim 2, wherein said iron oxide is magnetite, maghemite or a mixture thereof and said ferrite is an oxide of the formula (Fe,M)3O4, wherein M represents a transition metal ion.

4. The nanoparticle of claim 1, further comprising at least one additional agent.

5. The nanoparticle of claim 1, wherein said polymer is gelatin and said magnetic metal oxide is iron oxide.

6. The nanoparticle of claim 4, wherein said at least one additional agent is cRGD peptide or peptidomimetic.

7. A method for inducing apoptosis, autophagy, or both in a cancer cell, comprising the step of contacting said cell with a nanoparticle of claim 1.

8. The method of claim 7, further comprising Gamma irradiating said cell.

9. The method of claim 7, wherein said cancer cell is a glioma cell, a cancer stem cell, a carcinoma cell, a breast cancer cell, or a lung cancer cell.

10. The method of claim 7, wherein said inducing apoptosis, autophagy, or both in a cancer cell is treating a patient afflicted with cancer.

11. The method of claim 10, wherein said patient is afflicted with glioma, carcinoma, breast cancer or a lung cancer.

12. The method of claim 7, further contacting said cell with a proteasome inhibitor.

13. The method of claim 7, wherein said nanoparticle is non-toxic to a non-cancer cell.

14. A method for treating a subject afflicted with glioma, comprising the step of administering to said subject an effective amount of a composition comprising said nanoparticle of claim 1.

15. The method of claim 14, further comprising the step of administering to said subject a proteasome inhibitor.

16. The method of claim 14, wherein said nanoparticle is non-toxic to a non-cancer cell.

17. The method of claim 14, further comprising Gamma irradiating said glioma.

18. The nanoparticle of claim 1, wherein said nanoparticle is non-toxic to a non-cancer cell.

19. The nanoparticle of claim 1, further comprising a drug, a dye label, a contrast agent, or combination thereof.

20. The nanoparticle of claim 19, wherein said dye label is a fluorescent dye.

21. A composition comprising the nanoparticle of claim 1 and a pharmaceutical acceptable carrier.

22. A method for preparing a nanoparticle according to claim 1, comprising the following consecutive steps:
   a. mixing an aqueous solution comprising a soluble metal chelating polymer with at least one soluble metal salt;
   b. oxidizing metal ions formed in said solution;
   c. forming said nanoparticle in said solution by adjusting acidity of said solution to a basic pH;
   d. adding an additional portion of a metal salt to said solution;
   e. oxidizing metal ions formed in said solution;
   f. adjusting acidity of said solution to a basic pH;
   g. repeating steps (d) to (f) at least once;
   h. functionalizing said nanoparticle;
   i. contacting said functionalized nanoparticle with at least Apo-2L; and j. blocking remaining active sites on a surface of said nanoparticle.

23. The method according to claim 22, wherein said polymeric metal chelating agent comprises functional groups, wherein said functional groups comprise amino, hydroxyl, carboxylate, —SH, ether, immine, phosphate, and sulfide groups.

24. The method according to claim 22, wherein said polymeric metal chelating agent is gelatin, polymethylenimine, dextran, chitosan, polylysine, polyvinylpyrrolidone, or combination thereof.

25. The method according to claim 22, wherein said functionalizing said nanoparticle comprises contacting said nanoparticle with acryloyl chloride, divinyl sulfone (DVS), dicarbonyl immidazole, ethylene glycolbis (sulfosuccinimidylsuccinate), m-maleimidobenzoic acid N-hydroxysulfosuccinimide ester, or any combination thereof.

26. The method according to claim 22, wherein said functionalizing further comprises coating said nanoparticle with a coating polymer.

27. The method according to claim 26, wherein said functionalizing further comprises crosslinking said coating polymer with acryloyl chloride, divinyl sulfone (DVS), dicarbonyl immidazole, ethylene glycolbis (sulfosuccinimidylsuccinate), m-maleimidobenzoic acid N-hydroxysulfosuccinimide ester, or any combination thereof.

28. The method according to claim 22, wherein said aqueous solution comprises: a drug, a dye label, a contrast agent, or any combination thereof.

29. The method according to claim 22, wherein said soluble metal chelating polymer is bound to said Apo-2L.

30. The method according to claim 28, wherein said dye label is a fluorescent dye.

31. The method according to claim 29, wherein said magnetic metal oxide is bound to said Apo-2L.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: CYCLO
<222> LOCATION: (1)..(5)
<220> FEATURE:
```

```
<221> NAME/KEY: D-AMINO ACID
<222> LOCATION: (4)..(4)

<400> SEQUENCE: 1

Arg Gly Asp Phe Lys
1               5
```